US011718866B2

(12) United States Patent
Demokritou et al.

(10) Patent No.: US 11,718,866 B2
(45) Date of Patent: Aug. 8, 2023

(54) ENGINEERED WATER NANOSTRUCTURES (EWNS) AND USES THEREOF

(71) Applicant: President and Fellows of Harvard College, Cambridge, MA (US)

(72) Inventors: Philip Demokritou, Brookline, MA (US); Georgios Pyrgiotakis, Cranford, NJ (US); Joseph D. Brain, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/879,029

(22) Filed: Aug. 2, 2022

(65) Prior Publication Data

US 2023/0036792 A1 Feb. 2, 2023

Related U.S. Application Data

(62) Division of application No. 15/511,532, filed as application No. PCT/US2015/050460 on Sep. 16, 2015, now Pat. No. 11,479,799.

(Continued)

(51) Int. Cl.
*C12Q 1/02* (2006.01)
*A61L 2/00* (2006.01)
(Continued)

(52) U.S. Cl.
CPC ............. *C12Q 1/02* (2013.01); *A23L 3/32* (2013.01); *A23L 3/3409* (2013.01); *A23L 3/3463* (2013.01); *A23L 3/3481* (2013.01); *A61L 2/00* (2013.01); *A61L 2/03* (2013.01); *A61L 2/22* (2013.01); *A61L 9/14* (2013.01); *A61L 9/22* (2013.01); *C12N 1/20* (2013.01); *C25B 9/00* (2013.01); *A61L 2/0088* (2013.01); *A61L 2202/11* (2013.01); *A61L 2209/213* (2013.01);
(Continued)

(58) Field of Classification Search
CPC ........... C12Q 1/02; A23L 3/3463; C12N 1/20; A61L 2/22
USPC ....................................................... 426/665
See application file for complete search history.

(56) References Cited

U.S. PATENT DOCUMENTS 3,704,572 A 12/1972 Gourdine et al.
4,430,555 A 2/1984 Stokes
(Continued)

FOREIGN PATENT DOCUMENTS

EP 2226127 A1 9/2010
EP 3194609 B1 8/2019
(Continued)

OTHER PUBLICATIONS

"U.S. Appl. No. 15/511,532, Advisory Action dated Jan. 27, 2020", 5 pgs.
(Continued)

*Primary Examiner* — Donald R Spamer
*Assistant Examiner* — Philip A Dubois
(74) *Attorney, Agent, or Firm* — Schwegman Lundberg & Woessner, P.A.

(57) ABSTRACT

Various embodiments of the present invention relate to, among other things, systems for generating engineered water nanostructures (EWNS) comprising reactive oxygen species (ROS) and methods for inactivating at least one of viruses, bacteria, bacterial spores, and fungi in or on a wound of a subject in need thereof or on produce by applying EWNS to the wound or to the produce.

14 Claims, 8 Drawing Sheets

Related U.S. Application Data

(60) Provisional application No. 62/050,996, filed on Sep. 16, 2014.

(51) Int. Cl.

| | | |
|---|---|---|
| *A61L 2/03* | (2006.01) | |
| *A61L 2/22* | (2006.01) | |
| *A61L 9/14* | (2006.01) | |
| *A61L 9/22* | (2006.01) | |
| *C25B 9/00* | (2021.01) | |
| *A23L 3/3481* | (2006.01) | |
| *A23L 3/3409* | (2006.01) | |
| *A23L 3/32* | (2006.01) | |
| *A23L 3/3463* | (2006.01) | |
| *C12N 1/20* | (2006.01) | |
| *C02F 1/46* | (2023.01) | |

(52) U.S. Cl.
CPC ........ *C02F 1/4608* (2013.01); *C02F 2303/04* (2013.01); *C02F 2305/023* (2013.01)

(56) References Cited

U.S. PATENT DOCUMENTS

| | | | |
|---|---|---|---|
| 5,873,523 | A | 2/1999 | Gomez et al. |
| 6,136,763 | A | 10/2000 | Matsumoto et al. |
| 6,148,508 | A | 11/2000 | Wolk |
| 7,473,298 | B2 | 1/2009 | Suda et al. |
| 7,517,852 | B2 | 4/2009 | Walsh et al. |
| 7,651,926 | B2 | 1/2010 | Jacobson et al. |
| 8,247,406 | B2 | 8/2012 | Street et al. |
| 8,267,884 | B1 | 9/2012 | Hicks |
| 11,479,799 | B2 | 10/2022 | Demokritou et al. |
| 2009/0114747 | A1 | 5/2009 | Nakada et al. |
| 2010/0223944 | A1 | 9/2010 | Tsujimoto et al. |
| 2012/0245577 | A1 | 9/2012 | Mihalik et al. |
| 2013/0033861 | A1 | 12/2013 | Teslenko et al. |
| 2017/0298407 | A1 | 10/2017 | Demokritou et al. |

FOREIGN PATENT DOCUMENTS

| | | |
|---|---|---|
| WO | WO-2014136382 A1 | 9/2014 |
| WO | WO-2016044443 A1 | 3/2016 |

OTHER PUBLICATIONS

"U.S. Appl. No. 15/511,532, Advisory Action dated Mar. 21, 2022", 3 pgs.
"U.S. Appl. No. 15/511,532, Corrected Notice of Allowability dated Jul. 26, 2022", 3 pgs.
"U.S. Appl. No. 15/511,532, Final Office Action dated Feb. 18, 2021", 11 pgs.
"U.S. Appl. No. 15/511,532, Final Office Action dated Sep. 11, 2019", 8 pgs.
"U.S. Appl. No. 15/511,532, Final Office Action dated Dec. 20, 2021", 11 pgs.
"U.S. Appl. No. 15/511,532, Non Final Office Action dated Mar. 27, 2019", 9 pgs.
"U.S. Appl. No. 15/511,532, Non Final Office Action dated Jul. 10, 2020", 11 pgs.
"U.S. Appl. No. 15/511,532, Notice of Allowance dated Jun. 17, 2022", 8 pgs.
"U.S. Appl. No. 15/511,532, Pre-Appeal Brief Request for Review filed Apr. 20, 2022", 3 pgs.
"U.S. Appl. No. 15/511,532, Response filed Feb. 11, 2020 to Advisory Action dated Jan. 27, 2020", 11 pgs.
"U.S. Appl. No. 15/511,532, Response filed Feb. 22, 2022 to Final Office Action dated Dec. 20, 2021", 12 pgs.
"U.S. Appl. No. 15/511,532, Response filed Aug. 18, 2021 to Final Office Action dated Feb. 18, 2021", 11 pages.
"U.S. Appl. No. 15/511,532, Response filed Oct. 12, 2020 to Non Final Office Action dated Jul. 10, 2020", 11 pgs.
"U.S. Appl. No. 15/511,532, Response filed Dec. 11, 2019 to Final Office Action dated Sep. 11, 2019", 11 pgs.
"U.S. Appl. No. 15/511,532, Response filed Jun. 25, 2019 to Non-Final Office Action dated Mar. 27, 2019", 11 pgs.
"U.S. Appl. No. 15/511,532, Response to Restriction Requirement dated Jan. 11, 2019 filed Jan. 22, 2019", 10 pgs.
"U.S. Appl. No. 15/511,532, Restriction Requirement dated Jan. 11, 2019", 6 pgs.
"European Application Serial No. 15841524.0, Extended European Search Report dated Jun. 19, 2018", 11 pgs.
"European Application Serial No. 15841524.0, Partial Supplementary European Search Report dated Mar. 12, 2018", 12 pgs.
"European Application Serial No. 15841524.0, Response filed Jan. 15, 2019 to Extended European Search Report dated Jun. 19, 2018", 11 pgs.
"European Application Serial No. 19193737.4, Communication Pursuant to Article 94(3) EPC dated Sep. 17, 2020", 5 pgs.
"European Application Serial No. 19193737.4, Extended European Search Report dated Oct. 28, 2019", 7 pgs.
"European Application Serial No. 19193737.4, Response filed Jul. 22, 2020 to Extended European Search Report dated Oct. 28, 2019", 7 pgs.
"International Application Serial No. PCT/US2015/050460, International Search Report dated Dec. 18, 2015", 3 pgs.
"International Application Serial No. PCT/US2015/050460, Written Opinion dated Dec. 18, 2015", 22 pgs.
"Suppression effect of nanoe charged water particles on pet related allergens, bacteria, fungi and viruses have been verified. Technology and Design About Us Panasonic", Panasonic Corporation, (Feb. 20, 2012), 1-5.
Brain, et al., "Reactive Oxygen Species in the Killing of Pseudomonas aeruginosa by Human Leukocytes", Current Microbiology vol. 31, (1995).
Georgios, Pyrgiotakis, et al., "A chemical free, nanotechnology-based method for airborne bacterial inactivation using engineered water nanostructures", Environmental Science: NANO, vol. 1, No. 1, (Jan. 1, 2014), 15-26.
Groth, E, "Food Irradiation for Fresh Produce", Critical Issue Report irradiation for Fresh Produce, Retrieved from the Internet <https://organlc-center.org/reportfiles/IrradiationReport.pdP> on Nov. 11, 2015 (Nov. 11, 2015)., (Apr. 1, 2007), pp. 1-32.
Gutierrez, A A, "The science behind stable, super oxidized water. Exploring the various application of super-oxidized solutions", Wounds, (2006), 7-10.
Pandey, "Outcomes of superoxide solution dressings in surgical wounds: a randomized case control trial", Int J Biol Med Res. 2(4), (2011), 965-968.
Pyrgiotakis, "A chemical free, nanotechnology-based method for airborne bacterial inactivation using engineered water nanostructures", Environmental Science: Nano, iss. 1, (Nov. 28, 2013), pp. 15-26.
Pyrgiotakis, et al., "A novel method for bacteria inactivation using Engineered Water Nanostructures", <https://www.hsph.harvard.edu/nano/research/research-projects/140-2/>, (Oct. 20, 2012).
Pyrgiotakis, "Inactivation of Foodbome Microorganisms Using Engineered Water Nanostructures (EWNS)", Environmental Science & Technology, vol. 49, Iss. 06, (Feb. 19, 2015), pp. 3737-3745.
Pyrgiotakis, Georgios, et al., "Mycobacteria inactivation using Engineered Water Nanostructures (EWNS)", Nanomedicine: Nanotechnology, Biology, and Medicine, 10(6), (Aug. 1, 2014), 1175-1183.
Selgas, et al., "Attachment of Bacteria to Meat Surfaces: A Review", Meat Science, vol. 34. Iss. 03, (Jan. 1, 1993), pp. 265-273.
Sterflinger, et al., "Microbial deterioration of cultural heritage and works of art-tilting at windmills?", Applied Microbiology and Biotechnology, voi. 97, iss. 22, (Oct. 8, 2013), 9637-9646 pgs.
Xie, "Clinical study on the treatment of chronic wound with negatively-charged aerosollnt", J Clin Exp Med; 6(8), (2013), 649-654.
U.S. Appl. No. 15/511,532, filed Mar. 15, 2017, Engineered Water Nanostructures (EWNS) and Uses Thereof.

(56) References Cited

OTHER PUBLICATIONS

"European Application Serial No. 15841524.0, Response filed Oct. 20, 2017 to Communication Pursuant to Rules 161(2) and 162 EPC dated Apr. 25, 2017", 11 pgs.

"European Application Serial No. 19193737.4, Communication Pursuant to Article 94(3) EPC dated Mar. 18, 2021", 6 pgs.

"European Application Serial No. 19193737.4, Response filed Jan. 26, 2021 to Communicatin Pursurant to Article 94(3) EPC dated Sep. 17, 2020", 8 pgs.

"European Application Serial No. 19193737.4, Response filed Sep. 28, 2021 to Communication Pursuant to Article 94(3) EPC dated Mar. 18, 2021", 81 pgs.

"International Application Serial No. PCT/US2015/050460, International Preliminary Report on Patentability dated Mar. 30, 2017", 24 pgs.

ENGINEERED WATER NANOSTRUCTURES (EWNS) AND USES THEREOF

CROSS-REFERENCE TO RELATED APPLICATIONS

This application is a divisional of U.S. application Ser. No. 15/511,532, filed Mar. 15, 2017, which is a U.S. National Stage filing under 35 U.S.C. 371 from International Application No. PCT/US2015/050460, filed on Sep. 16, 2015, and published as WO 2016/044443 on Mar. 24, 2016, which claims priority to U.S. Provisional Appl. Ser. No. 62/050,996, filed Sep. 16, 2014, the entireties of which are incorporated by reference as if fully set forth herein.

BACKGROUND OF THE INVENTION

Very few chemical-free, nanotechnology-based methods are known for significantly reducing the microbial load on the surface of fresh produce or for significantly reducing the bacterial and/or viral loads in wounds to, among other things, facilitate or accelerate the wound healing process.
Fresh Produce Surfaces Cleaning and disinfection of the surface of foods, as well as the surfaces that the food contacts, is crucial in preventing foodborne disease. A number of different treatments are currently available for disinfecting the surfaces of whole and cut raw fruit and vegetables or their contact surfaces during production. These mainly include chlorine (elemental or as a hypochlorite); chlorine dioxide; peracetic acid; hydrogen peroxide; quaternary ammonium compounds for wash water; ozone (gaseous and aqueous); and irradiation.

A large number of these methods leave behind chemical traces, and in addition, are not compatible with organic food laws that completely ban the use of any chemical. In addition, most of these treatments cannot be relied upon to completely disinfect raw fresh produce, at least when administered at levels that will not cause deterioration in sensory quality (e.g., changes in texture, color, aroma, etc.). Even irradiation may not be completely effective in killing viruses on fruit and vegetables. Most washing and disinfection methods provide 90-99% population reduction and not 100%, as some would assume. Furthermore, none of these methods can be used continuously as a means to ensure safety of the product during its journey from farm to fork. The food industry is therefore in need of new approaches to deal effectively with emerging public health hazards and compatible with new "green" environmental approaches and consumer preferences.
Wound Surfaces Microbes are in constant interaction with biological surfaces such as the skin and mucus membranes which if compromised, as in the case of wounds, can cause serious, sometimes life threatening infections that delay wound healing, cause tissue damage, pain and discomfort. The toll of infectious disease is further complicated through the evolution and widespread of antibiotic resistant bacteria, while the constant antigenic shift of influenza viruses exemplifies the difficulties associated with vaccine development. Control of these infections remains a challenge and currently relies on interventions linked with significant shortcomings and health risks. Air disinfection approaches rely on using UV-A radiation, HEPA filtration and biocidal gasses for the interruption of the airborne transmission, while for the prevention of wound infections, use of chemicals such as topical antiseptics and systemic antibiotics is widespread. There is therefore a need for new chemical-free approaches to aid wound healing without, among other things, adding to the problem of bacterial antibiotic resistance.

BRIEF DESCRIPTION OF THE FIGURES

The drawings illustrate generally, by way of example, but not by way of limitation, various embodiments discussed in the present document.

DESCRIPTION

Figure 1:
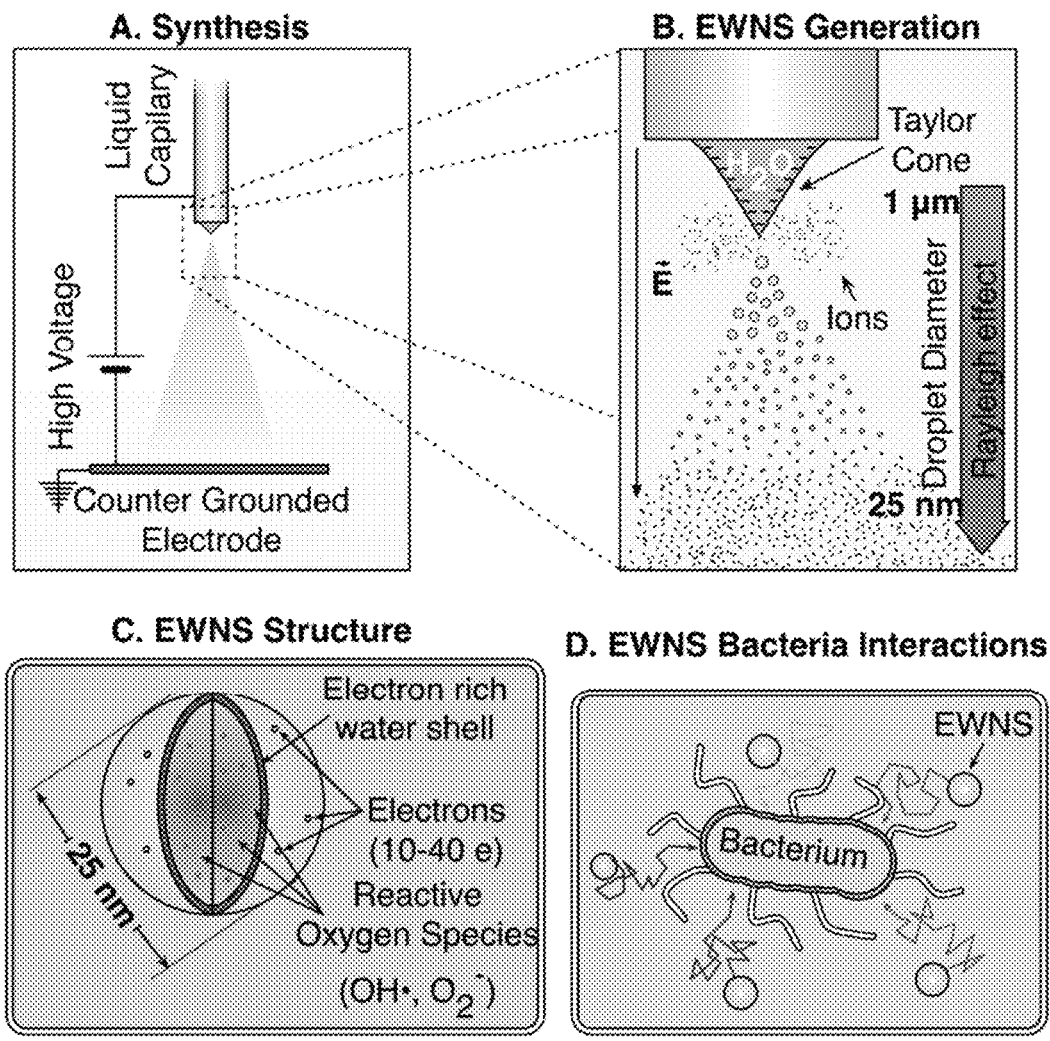
FIG. 1 is a schematic of a system for the synthesis of EWNS of the various embodiments of the present invention and their interactions with pathogens, in this case, bacteria.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

The various embodiments of the present invention provide, among other things, "chemical-free" approaches for significantly reducing the microbial load on the surface of fresh produce (e.g., raw or minimally processed fruit or vegetables) or for significantly reducing the bacterial and/or viral loads in wounds to, among other things, facilitate or accelerate the wound healing process. The various embodiments of the present invention achieve these goals by using engineered water nanostructures (EWNS) to reduce the microbial load on the surfaces of fresh produce and to significantly reduce the bacterial and/or viral loads on or in wounds such as chronic ulcers, skin diseases, skin burns, and the like.

It should be understood that, although the various embodiments of the present invention provide, among other things, "chemical-free" approaches for significantly reducing the microbial load on the surface of fresh produce or for significantly reducing the bacterial and/or viral loads in or around wounds, the methods described herein can also be used in conjunction with soap and water, as well as other chemical-based antiinfective methods, including topical antiseptics and systemic antibiotics.

Briefly, EWNS are generated, in some embodiments, by elctrospraying water from the tip of an electrode. A high voltage (e.g., 5 kV) is then applied between the two electrodes placed, e.g., about 5 mm apart. The strong electric field between the two electrodes causes negative charges to accumulate on the surface of the condensed water that is held on the electrode by surface tension. As a result, highly charged water droplets form and continue to break into smaller particles. At optimum conditions of water flow and electric field, EWNS can reach nanoscale size objects and possess unique physicochemical and morphological properties. EWNS are highly mobile due to their nanoscale size and remain suspended in the air for hours (extended lifetime) due to their increased surface charge which reduces evaporation. Concurrently with the generation of water droplets, the electric field conditions can be manipulated so that water molecules are split and electrons removed, resulting in a high number of reactive oxygen species (ROS) (ionization process). The concurrently generated, ROS are encapsulated in the EWNS. EWNS generated in this fashion are highly charged and carry an average of 10 to over 40 electron charges per nanostructure. In addition, the EWNS are loaded with at least two ROS species, namely, hydroxide radicals (OH.) and superoxide ($O_2^-$). ROS such as hydroxide radicals and superoxide are known for their ability to inactivate bacteria on surfaces, as occurs in $TiO_2$ photocatalysis. Electrospray properties, namely, electric field and water flow rate, can be optimized to result in EWNS that are polydisperse in size and exhibit a log normal distribution with a mean 25 nm, a mode of 23 nm and a standard deviation of 9 nm. Without wishing to be bound by any particular theory, it is believed that the polydispersity is due to the variation of the surface charge, the randomness of the Rayleigh effect, and the inevitable evaporation over time. In addition, EWNS generated in this fashion are stable in size with very minimal evaporation under ambient conditions (e.g., 25° C. and 1 atm).

The methods of the various embodiments of the present invention are directed to a method for inactivating at least one of viruses (e.g., the influenza virus, Norovirus, and Hepatitis A virus), bacteria, mycobacteria, bacterial spores, and fungi in a wound of a subject in need thereof, the method comprising: applying EWNS comprising reactive oxygen species (ROS) to the wound to inactivate the at least one of viruses, bacteria, and bacterial spores. Additionally, by controlling the wound microenvironment around the wound by constantly supplying EWNS, the wound healing process can be enhanced.

As used herein, the term "wounds" or "wound" generally refers to wounds resulting from trauma, a surgical procedure, an infectious disease or an underlying condition. The term "wounds" or "wound" encompasses open wounds as well as closed wounds, such as sutured or stapled wounds. Examples of open wounds include punctures, abrasions, cuts, lacerations, and burns. The term "wounds" or "wound" also encompasses chronic wounds, such as pressure ulcers, diabetic ulcers, arterial ulcers, venous ulcers or combination of all the above.

As used herein, the term "in a wound" refers to inside a wound, in the periphery of a wound or near a wound.

The methods of the various embodiments of the present invention are also generally directed to a method for inactivating at least one of viruses, bacteria, mycobacteria, bacterial spores, and fungi on unwounded tissue before the unwounded tissue is wounded by, e.g., surgery. The various methods of the present invention, therefore, provide methods for disinfection of tissue (e.g., skin) in general and, in particular, for disinfection of tissue prior to or during surgery.

Other method of the various embodiments of the present invention are directed to inactivating at least one of bacteria, mycobacteria, bacterial spores, fungi (e.g., yeasts and molds) on produce comprising: applying EWNS comprising ROS to the produce to inactivate the at least one of bacteria, mycobacteria, bacterial spores, and fungi. This method can also be extended to inactivating viruses on produce. And the method can be employed at at any point in the production of the produce; that is, from "field to fork."

As used herein, the term "produce" includes, but is not limited to, fruit and vegetables including: avocado and pome fruits such as apples and pears; nectarines and peaches; vegetables from the Solcanaceae family, for example, potatoes, peppers, eggplants and tomatoes; vegetables from the Alliaceae family, such as onions; vegetables from the Brassiaceae family also referred to as the Cruciferae family, for example cabbage; vegetables from the Cucurbitaceae family, for example, cucumbers; vegetables from the Apiaceae family also referred to as the Umbelliferae family, for example celery; the Compositae family, also referred to as the Asteraceae family, for example, lettuce; and edible fungi of the Ascomycetes/Basidiomycetes classes.

Even though the methods of method for inactivating at least one of bacteria, mycobacteria, bacterial spores, and fungi described herein can be applied to produce, they can also be applied to inactivating at least one of bacteria, mycobacteria, bacterial spores, and fungi on other food including, but not limited to, meat (e.g., beef, chicken, and pork) and other foodstuffs at any point in its production; that is, from "field to fork."

As used herein, the term "reactive oxygen species" and "ROS" generally refers to any reactive oxygen species that can be generated in water droplets using the EWNS generating methods described herein. ROS therefore include, but are not limited to, hydroxide radicals (OH.) and superoxide ($O_2^-$).

As used herein, the term "bacteria" generally refers to gram-positive and gram-negative bacteria. Gram-positive bacteria include, but are not limited to, mycobacteria. Mycobacteria, in turn, include, but are not limited to, *M. africanum, M. avium, M. bovis, M. chelonei, M. farcinogenes, M. flavum, M. fortuitum, M. haemophilum, M. intracellulare, M. kansasii, M. leprae, M. lepraemurium, M. marinum, M. microti, M. parafortuitum, M. paratuberculosis, M. phlei, M. scrofulaceum, M. senegalense, M. simiae, M. smegmatis, M. thermoresistibile, M. tuberculosis, M. ulcerans*, and *M. xenopi*. Other gram-positive bacteria include, but are not limited to, gram-positive cocci including *Staphylococcus aureus*, methicillin-resistant *Staphylococcus aureus* (MRSA), Group A Streptococci, Group B Streptococci, Group C Streptococci, Group G Streptococci, and vancomycin resistant Enterococci (VRE). Other gram-positive bacteria include *Listeria* bacterial strains (e.g., *Listeria monocytogenes*), *Clostridium* bacterial strains (e.g., *Clostridium perfigens* and *Clostridium botulinum*), and *Bacillus cereus.*

Gram-negative bacteria include, but are not limited to, *Pseudomonas aeruginosa, Pseudomonas* spp., *Serratia marcescens*, and *Pseudomonas aeruginosa*. Other gram negative bacteria include *E. coli, Salmonella* bacterial strains, and *Campylobacter jejuni, Shigella*, and *Vibrio*.

As used herein, the term "yeasts" generally refers to organisms such as *S. cerevisiae* and the like from the fungi family.

As used herein, the term "subject" generally refers to a human, non-human primate, rat, mouse, cow, horse, pig, sheep, goat, dog, cat, etc. In some embodiments, the subject is preferably a human subject.

In some embodiments, the EWNS are applied to a wound, produce or meat at a concentration of about 5,000 to about 500,000 EWNS per mL of air surrounding or around the wound, produce or meat. In some embodiments, the EWNS are applied to a wound, produce or meat at a concentration of about 5,000 to about 100,000 EWNS per mL, about 5,000 to about 10,000; about 5,000 to about 50,000; about 10,000 to about 50,000; about 25,000 to about 100,000; or about 5,000 to about 25,000 EWNS per mL.; about 100,000 to about 500,000; about 500,000 to about 1,000,000 EWNS per mL; about 17,000 to about 24,000 EWNS per mL; or about 42,000 to about 60,000 EWNS per mL (e.g., EWNS per mL of air surrounding or around the wound, produce or meat, as described herein).

In some embodiments, when the EWNS are applied to a wound, produce or meat at the aforementioned concentration(s), the application results in 1 $\log_{10}$ to about a 3 $\log_{10}$ reduction in the cfu, compared to control. In some embodiments, the number of colony forming units (cfu) present on the wound, produce or meat is reduced by about 1 $\log_{10}$ to about 8 $\log_{10}$; about 1 $\log_{10}$ to about 5 $\log_{10}$; about 1 $\log_{10}$ to about 6 $\log_{10}$; 2 $\log_{10}$ to about 6 $\log_{10}$; about 1 $\log_{10}$ to about 1.5 $\log_{10}$; about 1.5 $\log_{10}$ to about 3 $\log_{10}$; about 2 $\log_{10}$ to about 3 $\log_{10}$; about 1 $\log_{10}$ to about 2.5 $\log_{10}$; or about 1 $\log_{10}$ to about 2 $\log_{10}$, compared to control.

The EWNS of the various embodiments of the present invention can be applied to a wound, produce or meat for any suitable time period over which a suitable $\log_{10}$ reduction in the number of cfu is observed. Examples of suitable time periods over which a suitable $\log_{10}$ reduction in the number of cfu is observed include about 30 seconds to about 5 hours; about one minute to about 20 minutes; about 10 minutes to about 180 minutes (3 hours); about 1 hour to about 5 hours; about 30 seconds to 5 minutes; about 1 hour to about 3 hours; or about 30 minutes to 1 hour.

In some embodiments, when the EWNS are applied to a wound, produce or meat at the aforementioned concentration(s) (e.g., from about 30,000 EWNS per mL to about 50,000 EWNS per mL), the application results in $\log_{10}$ cfu removal rates of from about 1 $\log_{10}$/h to about 8 $\log_{10}$/h, compared to control. In some embodiments, the $\log_{10}$ cfu removal rates on the wound, produce or meat is from about 1 $\log_{10}$/h to about 6 $\log_{10}$/h; about 1 $\log_{10}$/h to about 5 $\log_{10}$/h; 2 $\log_{10}$/h to about 6 $\log_{10}$/h; about 1 $\log_{10}$/h to about 1.5 $\log_{10}$/h; about 1.5 $\log_{10}$/h to about 3 $\log_{10}$/h; about 1 $\log_{10}$/h to about 3 $\log_{10}$/h; about 1 $\log_{10}$/h to about 2.5 $\log_{10}$/h; or about 1 $\log_{10}$/h to about 2 $\log_{10}$/h, compared to control.

In some embodiments, the electric charge of the EWNS of the various embodiments of the present invention is from about 10 to about 100 e−; about 10 to about 25 e−; about 20 to about 50 e−; about 40 to about 80 e−; or about 10 to about 30 e−.

The EWNS of the various embodiments of the present invention can be applied to a wound, produce or meat using any suitable means including, but not limited to electrostatic precipitation or diffusion, or a combination of both using any suitable method, including the methods described herein.

Other method of the various embodiments of the present invention are directed to inactivating at least one of viruses, bacteria, mycobacteria, bacterial spores, and fungi on any surface that cannot otherwise be disinfected using conventional methods (e.g., chlorine; chlorine dioxide; peracetic acid; hydrogen peroxide; quaternary ammonium compounds for wash water; ozone; and irradiation) because such conventional treatment could cause damage to the surface. Such surfaces include any surfaces on or around works of art, archaeological artifacts, museum artifacts, and the like.

Other method of the various embodiments of the present invention are directed to inactivating at least one of viruses, bacteria, mycobacteria, bacterial spores, and fungi on any surface including cloth (e.g., in clothes), medical products (e.g., gauze and tape); medical instruments; medical devices; etc.

The EWNS of the various embodiments of the present invention can be generated by any suitable method known in the art and using any suitable electro spray device known in the art, including the methods and devices described herein. One method and device known in the art for the generation of EWNS are described in U.S. Pat. No. 7,473,298, which is incorporated by reference as if fully set forth herein.

FIGS. 2A-2C depict aspects of a system 200 for generating EWNS and, optionally, applying EWNS to a target, in an example embodiment.

FIG. 2A depicts the system 200 generally. A fluid source 202 is configured to contain fluid 204, such as water as disclosed herein. A source of pressure 206 is configured to place the fluid 204 in the fluid source 202 under pressure, forcing the fluid 204 up a tube 208 to a fluid emitter 210.

The fluid emitter 210 includes a conduit 212 fluidly coupled to the fluid source 202. In various examples, the conduit 212 is a capillary, needle, or other elongate tube that includes a lumen through which fluid 204 from the fluid source 202 may pass. In various examples, the conduit 212 is a metallic capillary or metallic needle or is made of any of a variety of electrically conductive substances. The conduit 212 includes an aperture 214 through which the fluid 204 exits the conduit 212.

The conduit 212 is positioned with respect and in relation to an electrode 216. In FIG. 2B, the conduit 212 is shown to be at a 0 degree angle with regard to vertical axis 224 and at a 90 degree angle with regard to the electrode 216. But the conduit 212 can be positioned at any suitable angle in relation to vertical axis 224 (e.g., ±45 degrees). Fluid 204 that exits the conduit 212 via the aperture 214 comes into proximity of the electrode 216. A variable voltage source 218 is coupled between the conduit 212 and the electrode 216 to induce an electric potential between the conduit 212 and the electrode 216. Fluid 204 that passes through the conduit 212 and in proximity of (including potentially in contact with) the electrode 216 is energized and changes state to EWNS, as disclosed herein. The EWNS is then collected in a fluid collection member 220.

FIG. 2B is a detailed depiction of aspects of the system 200. As illustrated, the conduit 212 has a first end coupled to the fluid emitter and a second end opening up with the aperture 214 and is positioned above the electrode 216. The aperture 214 is directly above an electrode aperture 222 in the electrode 216 along a vertical axis 224. In the illustrated example, the electrode aperture 222 is circular having a diameter D, though in various examples the electrode aperture 222 may have any of a variety of shapes and sizes as desired. In some instances, the diameter D can be changed to enhance the field strength from about 1% to about 10% as the diameter is changed.

A distance between the aperture 214 and the electrode 216 defines a distance L. The distance L is predetermined and adjustable based on a relative position of the aperture 214 with respect to the electrode 216. In various examples, either or both of the conduit 212 and the electrode 216 are repositionable or adjustable. Thus, the distance L may be adjusted by repositioning one or both of the conduit 212 and the electrode 216.

While the distance L is depicted as being along the vertical axis 224, it is noted and emphasized that the distance L may have a horizontal component, in part or in whole. In various examples, the source of pressure 206 may be such that fluid 204 is expelled from the aperture with sufficient force that the fluid 204 may travel a horizontal distance from the aperture 214 before coming in proximity of the electrode 216, in which case the distance L may include a horizontal component.

The applied voltage V from the voltage source 218 and resultant electric potential between the conduit 212 and the electrode 216, the distance L, the electrode aperture 222 diameter D, and the flow rate of the fluid 204 through the aperture 214 may all be adjustably varied to generate nanoscale size EWNS. Those components may be adjusted to seek to impart a relatively high charge and ROS content to the EWNS.

The system 200 generates an electric field between the conduit 212 and the electrode 216. The strength of the electric field is related to the applied voltage V; the distance L; and the overall geometry of the electrode 216 and the electrode aperture 218. In some embodiments, the electric field strength is from about $1\times10^5$ V/m to about $6\times10^5$ V/m; e.g., from about $1.5\times10^5$ V/m to about $5\times10^5$ V/m; about $2\times10^5$ V/m to about $4.5\times10^5$ V/m; or about $2\times10^5$ V/m to about $5\times10^5$ V/m.

Figure 2:
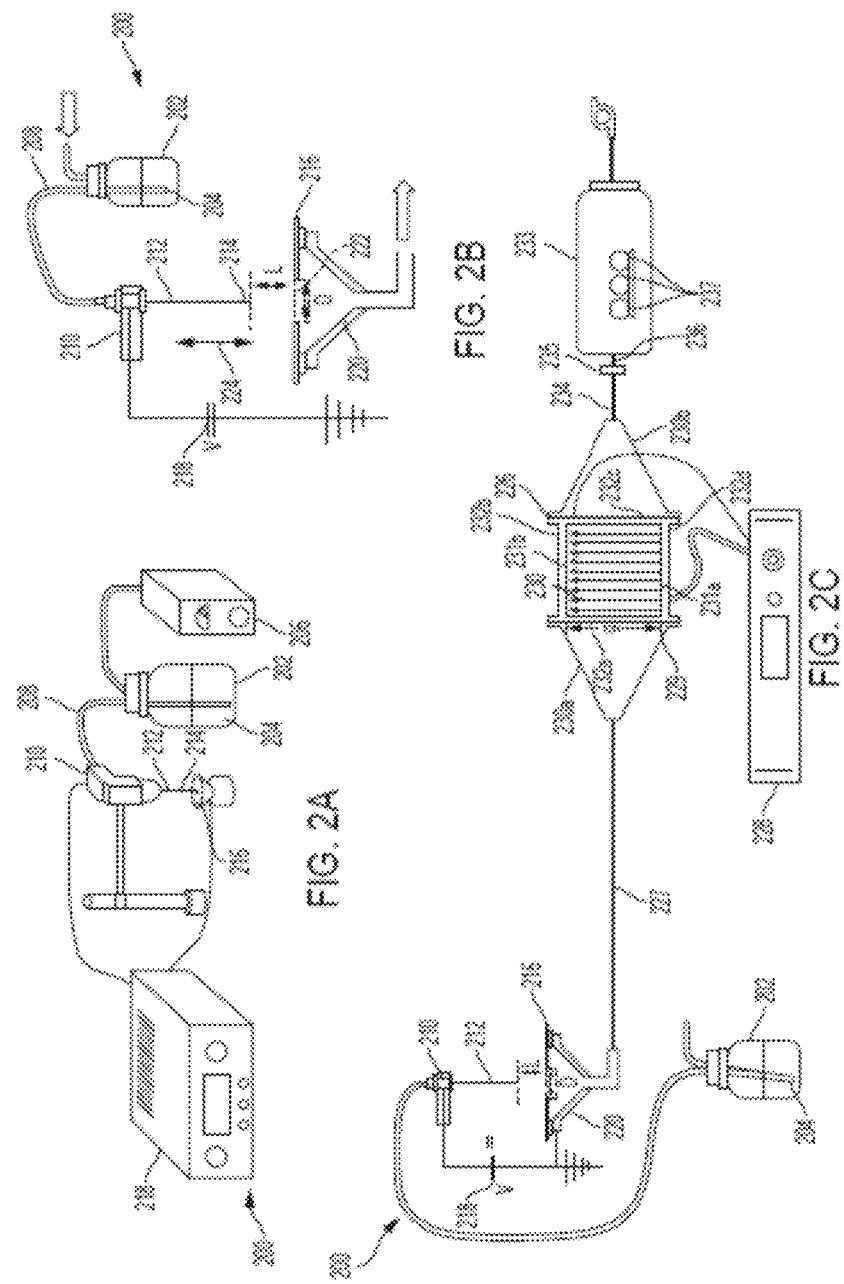
FIGS. 2A-2C depict aspects of a system 200 for generating EWNS and, optionally, applying EWNS to a target, in an example embodiment for pathogen inactivation.

FIG. 2C depicts a test and/or application setup of the system 200, in an example embodiment. The EWNS collected by the fluid collection member 220 is provided to an electrostatic precipitator exposure system (EPES) 226 via conduit 227. An EPES voltage source 228 creates an electric field 230 to cause the EWNS to be deposited on a target (not shown). As discussed herein, the EWNS can be applied to any target, including a wound, produce or meat (or any other surface of interest) using a diffusion exposure approach or an electrostatic precipitation exposure approach using, e.g., an electrostatic precipitation exposure system (EPES) such as the one depicted in FIG. 2C. In some embodiments the deposition/applying efficiency is from about 50% to about 100% (e.g., from about 50% to about 90%; about 80% to about 99%; or about 90% to about 100%) with 3 kV voltage and 0.5 L/min flow rate. In other embodiments the deposition/applying efficiency is from about 50% to about 100% (e.g., from about 50% to about 90%; about 80% to about 99%; or about 90% to about 100%) with 5 kV voltage and 0.5 L/min flow rate. As used herein, the term "deposition/applying efficiency" refers to the percentage of EWNS generated that are deposited/applied to the a wound, produce or meat or surface of interest.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about" as used herein can allow for a degree of variability in a value or range, for example, within 10%, within 5%, or within 1% of a stated value or of a stated limit of a range.

The term "does not cause substantially any deterioration in the sensory quality of the produce" refers to about 20% to about 1%; about 15% to about 1%; about 10% to about 1%; about 5% to about 1%; or about 2% to about 1% deterioration in the sensory quality of the produce. The term "does not cause any deterioration in the sensory quality of the produce" refers to 0% deterioration in the sensory quality of the produce, using methods known in the art for determining the deterioration in the sensory quality of the produce.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following examples which are offered by way of illustration. The present invention is not limited to the examples given herein.

Example 1: EWNS Generation

The EWNS are synthesized via electrospray, a method used to aerosolize particles and fibers from liquid suspensions according to the method described in Pyrgiotakis, G., et al., *Nanomedicine* 10: 1175-1183 (2014), which is incorporated by reference as if fully set forth herein. Electrospray relies on a strong electric field to aerosolize a liquid, which is contained in a fine metal capillary. The strong electric field causes the liquid to break into highly charged droplets. This phenomenon, known widely as Rayleigh effect, states that a liquid droplet with high surface charge density is unstable. The droplets continuously break down to the point where the surface charge is low enough to stop the continuous breaking of the droplets.

In brief, a gold plated electrode is cooled down to 6° C. via a Peltier element. The atmospheric water vapor, condensed on the electrode, becomes the source of water for the electrospray. High voltage of approximately 5 kV is applied between the Peltier electrode and a grounded counter electrode causing the water to break into small droplets. The operational environmental conditions were maintained at 20-25° C. and 45-55% Relative Humidity (RH).

In addition to the utilization of the modules, a EWNS generation system was developed to offer a stream of variable concentration at different flows. The EWNS generation consisted of an array of modules/needles was used to generate the EWNS. The modules were housed in a plastic chamber under controlled relative humidity conditions. The humidity was adjusted between 45-50% by a mixture of humidified air (HEPA filtered air through a bubbler) and a dried air (HEPA filtered air through DryRite). Organic free, deionized (DI) water (18.1 MΩ-cm, purified with Barnstead Nanopure, Thermo Scientific, Rockford, Ill.) was used in the synthesis of the EWNS. The generated ozone was removed by passing the aerosol through three freshly coated, glass honeycomb denuders. The denuders were coated with a solution of 140 mL of DI water, 5 g of $NaNO_3$, 5 g of $Ca_2CO_3$ and 5 g of glycerol. After the coating, the denuders were placed on paper towels to remove excess solution and are then left to dry for 24 hours under refrigeration. For each experiment fresh denuders were used. Regardless of the flow through the chamber the sampling flow from the EWNS generator was kept at 5 L/min to maximize the yield.

Example 2: Pathogen Inactivation on Skin

*Pseudomonas aeruginosa* is an opportunistic pathogen that may cause skin and other infections under favorable conditions. Bacteria are grown overnight (18 hours at 37° C.) in a broth culture in the presence of 100 μCi of radioisotope of iron ($^{59}Fe$) as a tracer. Growing bacteria incorporate $^{59}Fe$ resulting in radiolabeled suspension of *P. aeruginosa*. This suspension is used in an ex vivo assay to determine how much radiolabeled bacteria adhere to excised skin with or without prior exposure to EWNS aerosols. The broth culture is centrifuged at 3000 g for 30 min.. Then the bacterial pellet will be washed three times with sterile cold phosphate buffered saline (PBS) to remove unincorporated $^{59}Fe$ in the suspension. Based on previously determined optical density (of suspension)-colony forming unit (cfu) correlation, a bacterial suspension with $OD_{620nm}$=0.7 (~1.6× 108 cfu/mL) is prepared. Several dilutions of the suspension are tested.

Rats are euthanized, the back skin is shaved, and cleaned with saline to remove dirt and loose skin layer. Pig-skin samples are obtained from Beth Israel Deaconess Medical Center. A 1×1 inch square of skin sample is removed, placed on a petri dish, and exposed to EWNS or filtered air for 5, 15 or 30 min. Then, the skin samples are immersed in a cold suspension of radiolabeled bacteria at 4° C. for an hour. Followed by gentle rinsing with cold PBS and blot-drying to remove excess PBS, before placing in pre-weighed tubes for gamma counting. The results of radioactivity measurements are expressed as nCi/g tissue. This radioactivity concentration are used as an estimate of residual bacteria remaining in each sample. Standard pour-plate technique is performed to estimate the number of colony forming units (cfu)/mL of bacterial suspension. Specific activity of $^{59}Fe$ (nCi/unit bacteria or cfu/nCi $^{59}Fe$) is estimated.

A culture preparation of *Pseudomonas aeruginosa* is prepared as above, except without adding $^{59}Fe$. The broth culture is prepared similarly to obtain a bacterial suspension with $OD_{620nm}$=0.7. Likewise, several dilutions are tested.

The rat and pig skin samples are prepared as described above. Then, the skin samples are immersed in a cold suspension of bacteria for an hour, followed by careful blot-drying to remove excess liquid. Randomly selected skin samples are exposed to EWNS aerosols or filtered air for various periods of time. After exposure, the outside surfaces of the skin samples is rinsed with sterile PBS to remove remaining bacteria on the surface. Standard pour-plate technique is performed to estimate the number of colony forming units (cfu)/mL of the PBS rinse. Reductions in cfu indicate bacterial inactivation.

Example 3: Pathogen Inactivation on Stainless Steel and Produce

Introduction

The assessment of EWNS inactivation on produce was performed under two distinct exposure approaches. In the first approach, the inoculated surfaces were exposed in an atmosphere containing the EWNS and the nanostructures were allowed to reach and interact with the surface via diffusion. In the second approach, an in-house built electrostatic precipitation exposure system (EPES) was used to take advantage of the EWNS high surface charge and an electric field to directly deposit the particles on the subjects (fruits, wounds, etc).

Diffusion Based Exposure Approach

A 40 L plastic chamber was used to house four EWNS electrospray modules. The modules were fixed from a shelf with downwards orientation at a distance of 5 cm from the inoculated surfaces. The humidity in the chamber was maintained at 45-50% by the influx of humidified air in the chamber generated by passing the environmental air through a water bubbler. The chamber air was mixed well by a small fan fixed on the upper space of the chamber. The temperature and the humidity inside the chamber were closely monitored. The current of devices and their voltages were monitored in real time to make sure they were functioning properly. A real time aerosol concentration system was also used to measure the number concentration over the exposure time (Ptrack, TSI, Shoreview, Minn.) in the environmental chamber. It has to be mentioned here that the EWNS number concentration, it is not the number that interacted with the bacteria. Since the transportation of the EWNS are via diffusion this is not possible to directly measure. However the particle number was monitored to avoid variation among experiments.

Delivery by Electrostatic Precipitator

The EPES system consists of a PVC chamber, which houses the electrostatic precipitation apparatus. The chamber has a front-loading door that allows the test surfaces to be placed on a plastic rack that keeps them elevated from the lower plate in order to avoid interference from the high voltage. The walls of the chamber were coated with aluminum foil that was grounded to prevent loses and eliminate reaction of any ozone present with the wall material. Further around the plates, Teflon® sheets were placed to eliminate the possibility of electrical discharge between the grounded walls and the plate held a high potential. The door and other seams were secured with screws and wingnuts, while the seams were kept airtight with compressible closed cell structure foam. The chamber was repeatedly tested at high pressures for air leaks.

The electrostatic precipitation apparatus (EPES) contains two metal parallel plates at distance of about 15.24 cm from each other that are connected to an external high voltage source. The bottom plate is always set to positive voltage and the top plate is always set at ground (floating ground). The voltage difference can be modulated to be between 0-10 kV resulting in an electric field up to 6.66 kV/m. The chambers inlet and outlet was constructed in a pyramid like shape to allow non-turbulent flow of the aerosol. The EPES was connected to the EWNS generation system that was described above. The electric field will drive the negatively charged EWNS on the inoculated produce, which are placed on a plastic rack at the edge of the bottom plate towards the incoming flow. For the specific geometry of the EPES and the EWNS charge a voltage difference of 3 kV is sufficient to deposit the particles on the lower plate.

Microbiological Procedures

Test Microorganisms

The following three bacteria were chosen for inoculation on test surfaces: *Escherichia coli* (ATCC #27325), a known fecal indicator and a surrogate to enteropathogenic strains; *Salmonella enterica* (ATCC #53647), a pathogen and surrogate to other pathogenic *Salmonella* strains, and *Listeria innocua* (ATCC #33090), an environmental indicator and surrogate to pathogenic *Listeria monocytogenes*. All strains were obtained from ATCC (Manassas, Va.). Stock cultures were maintained in glycerol at −80° C. Stock cultures were maintained on tryptic soy agar plates in the laboratory. For each experiment, the strains were cultured by transferring a single colony from previously seeded plates to 5 mL of tryptic soy broth (Becton Dickinson, Franklin Lakes, N.J.) and grown for 18 hours in a shaking water bath at 37° C.

Bacterial Inoculum Preparation

For stainless steel coupon experiments, the *E. coli* test suspension was prepared by concentrating the overnight culture in 1×PBS. A high concentration of *E. coli* (~1010 cfu/mL) was used since *E. coli* was particularly sensitive to air-drying on the stainless steel surface. For the produce (e.g., tomatoes) experiments, *E. coli* was not concentrated since it was not as susceptible to air-drying. *S. enterica* and *L. innocua* test suspensions were prepared by re-suspending 1 mL of overnight culture in 1 mL of 1×PBS. The concentration of the re-suspended culture was ~109 cfu/mL.

Test Surfaces

Two different surfaces were selected for inoculation due to the high relevance to the food industry, namely, stainless steel, which represents the most common food preparation surface; and tomato, which is a popular vegetable, consumed raw, and has been implicated in foodborne illness, in the United States and other parts of the world.

Stainless steel coupons: Stainless steel coupons (Stainless Steel Supply, N.C.) with a mirror finish, cut to a size of 1×1 $cm^2$ were used for the inactivation experiments. Prior to use, the coupons were wiped with 70% (v/v) ethanol and autoclaved. The coupons were then inoculated with selected bacterial suspensions as described herein.

Tomatoes: Organic grape tomatoes were bought from Whole Foods Market and stored at 4° C. until use. The tomatoes were washed thoroughly in a dilute soap solution and rinsed three times in deionized water before use. As with the stainless steel surfaces, tomatoes were surface inoculated with the selected bacterial populations.

Inoculation of Surfaces with Bacterial Suspensions

Bacterial inoculation took place in a CleanSpot PCR/UV Work Station (Coy Laboratory Products, Grass Lake, Mich.). Test suspensions (10 μL each) was added on each surface (stainless steel or tomato surface) and air dried (~15 minutes) at room temperature (~25° C.). Once the surfaces were dry, a random subset was chosen for immediate recovery of bacteria—(this was the time zero treatment)—to assess the loss due to air-drying. Nine coupons or tomatoes were immediately used for the EWNS inactivation experiments as described herein.

Recovery and Culturing of Bacteria from Stainless Steel and Tomato Surfaces

At each time point, the stainless steel coupons or tomatoes were removed from the two exposure chambers and processed. Each stainless steel coupon was transferred into a 50-mL beaker containing 1 mL 1×PBS and rinsed using an analog vortexer (VWR, Radnor, Pa.) at medium speed for 30 seconds. Similarly, each tomato was transferred to a 50 ml sterile conical polypropylene tube (VWR, Radnor, Pa.) containing 20 mL 1×PBS and rinsed using an analog vortexer (VWR, Radnor, Pa.) at medium speed for 30 seconds.

The rinsate was serially diluted and dilutions were plated on tryptic soy agar (Becton Dickinson, Franklin Lakes, N.J.) using the drop-plate method. Each agar plate was divided into quadrants. Five 10-μL drops of each dilution were dropped onto each quadrant, making a total of 20 drops on one plate. Plates were then incubated for 24-48 hours at 37° C. prior to colony counting, which was done manually.

Deposition Efficiency of the EPES System

At the time before the voltage activation the EWNS deposition rate represents the losses inside the chamber, which are inevitable and amount to only 3-5%. At t=90 s the high voltage is activated and the deposition gradually increases. This deposition is due to the electric field that is created between the two plates. The time required for the deposition to reach equilibrium sometimes depends on the flow through the chamber. After approximately 3 minutes, the deposition is reaching a maximum and steady value of approximately 62% which results in a neat deposition, due to the electric field, of approximately 58%. The deposition rate depending on the condition (flow through chamber and voltage) varies from 40% to 60%. The maximum achieved deposition of 58% was associated with 3 kV voltage and 2 L/min flow rate.

The electrostatic precipitator has low particle loses which are in the order of 5% regardless of the flow through the chamber. The application of the electric field has a positive effect on the deposition of the EWNS, which results in a higher deposition reaching up to 58%. For a flow of 2 L/min and a charge of 10 e it is estimated that 3 kV will be enough to deposit all of the EWNS. However, as has been shown in the past, the EWNS have a distribution of charges ranging from 1 to 40 e per structure with an average of 10 e. In this respect, deposition in the rate of 50% is in agreement with the expectations.

Further, the time required for the equilibrium is approximately three air changes. Similar is the response of the EWNS when the electric field is being turned off. The deposition may depend both on the flow through the chamber and on the electric field that is applied. However, at higher flows through the chamber the sensitivity to the electric field diminishes since the deposition is mostly depended on the flow. The optimal conditions were determined to be the 2 L/min flow and 3 kV voltage between the two plates for this particular geometry.

Inactivation of Bacteria on Stainless Steel and Tomato Surfaces

Diffusion Exposure Approach (Conditioning the Microenvironment of the Subject by Constantly Supplying EWNS Around the Subject Surfaces)

On stainless steel coupons all three bacteria (*Escherichia coli, Salmonella enterica*, and *Listeria innocua*) showed approximately 1.7 log reductions, as compared to control, after exposure to a EWNS treatment in the range of 24,000 of EWNS per mL of air, delivered by diffusion, between 45 to 90 min. More specifically, *E. coli* was susceptible to air-drying on the stainless steel coupons and therefore the inactivation was documented for only 45 minutes, at ten-minute intervals. After 30 minutes of exposure, the results show an approximate 1.8 log removal for 17,000-24,000 EWNS per mL of air, which represents an average removal rate of 0.067 logs/min while the control showed 0.0067 logs/min. This represents a rate of inactivation ten times as fast as the control. *Salmonella* exposed to EWNS was reduced by 0.8 logs in 90 minutes for 17,000-24,000 EWNS per mL of air, as compared to the control, which represents a removal rate of 0.018 logs/min while the control was reduced by 0.01 logs/min. The *Salmonella* inoculated stainless steel coupons exposed to EWNS had an 80% higher removal compared to the control. Finally, similar results were obtained for *Listeria* with an average 0.9 logs removal in 90 minutes for 17,000-24,000 EWNS per mL of air, as compared to the control, which represents a removal rate of 0.02 logs/min while the control showed 0.01 logs/min. It is worth pointing out that at higher EWNS exposure levels as determined by the EWNS particle concentration in the air, higher log reductions would be expected EWNS-driven inactivation of the bacteria on stainless steel coupons indicated that *E. coli* reduction was nearly 1.8 logs CFU, compared to the control, when data were extrapolated to include a 60 minutes time point for an air exposure level of 17,000-24,000 EWNS per mL of air particles per mL of air. Experiments in which *Listeria* and *Salmonella* were tested demonstrated 0.7 log reduction, compared to the control minutes for 17,000-24,000 EWNS per mL of air. Current effective treatments for disinfection of stainless steel surfaces include the use of chlorine-based compounds and quaternary ammonium compounds. Chlorine-based compounds are traditionally used because of the short contact time required for efficient disinfection. However, these compounds can also cause pitting and corrosion of stainless steel surfaces. Pitting, especially, can cause the formation of crevices, which are excellent niches for microorganisms to hide in and avoid disinfection. Therefore, the technology described in the current study is a promising alternative in terms of both efficacy as well as safety.

*E. coli* was able to survive air drying much better when inoculated on tomato surfaces. After 90 minutes, the results show an approximate 0.8 logs removal, as compared to the control, representing an average removal rate of 0.02 logs/min while the control showed 0.01 logs/min for minutes for 17,000-24,000 EWNS per mL of air. Similarly, for *Salmonella*, an average 1.5 logs removal, as compared to the control for minutes for 17,000-24,000 EWNS per mL of air, in 90 minutes was obtained, which represents a removal rate of 0.014 logs/min, while the control showed 0.008 logs/min. Finally, similar results were observed with *Listeria*, with an average 0.7 logs removal in 90 minutes 17,000-24,000 EWNS per mL of aiR. This represents a removal rate of 0.014 logs/min while the control showed 0.006 logs/min.

Compared to the stainless steel coupons, the tomato surface seemed less hostile to bacterial survival. This may be due to the differences in the properties of the two surfaces, leading to higher recovery numbers of all three bacteria from the control tomatoes. The successful recovery of the bacteria established that the method used was appropriate for the tomato experiments. The losses in the control treFIGSatment were all consistently within the limit of 1 log cfu, compared to the time zero concentration. Reports in the literature indicate that at 40% RH, the populations of *E. coli, Salmonella* and *Listeria* on cherry tomatoes were reduced by >2 log cfu/cm$^2$ after 1 hour. Additionally, there is evidence that at 90% RH, there was no reduction in population sizes, indicating the important role played by RH in pathogen survival.

EWNS-driven inactivation of the bacteria on tomatoes indicated that *E. coli* reduction was 0.9 logs cfu, compared to the 17,000-24,000 EWNS per mL of ai. Experiments in which *Listeria* and *Salmonella* were tested demonstrated 0.5 and 0.8 log reduction respectively 17,000-24,000 EWNS per mL of ai, compared to the control. Currently available treatments, such as chlorine dioxide, provide good microbial control at low concentrations and minimal exposure times. However, the control is most effective in water or on wet surfaces. When bacteria were dried on to tomato surfaces, the recommended dose of 5-10 ppm and exposure time of one minute did not produce an observable reduction in bacteria concentration. In a study on cucumbers, the researchers reported that a high concentration of $ClO_2$ (105 ppm) was unable to significantly reduce the microbial populations. Taking into account these results, the potential ill effects of the treatment on the produce, as well as potential toxicity effects on the handlers, the use of chlorine dioxide is not ideal.

In comparison, the EWNS treatment is safe and does not cause any damage to the produce, nor does it cause any or any substantial deterioration in sensory quality (e.g., changes in texture, color, aroma, etc.) of the produce. The results obtained in the current study suggest that a higher dose of the EWNS (increased concentration of particles as well as longer exposure times and the use of more effective delivery approach via electrostatic precipitation) would bring about higher inactivation potential in bacterial numbers than the one documented here.

Inactivation of Bacteria Via the EPES System

Tomatoes exposed to EWNS aerosol via diffusion without the electric field was at the same inactivation level as the control with a removal rate of 0.009 logs/min for 42,000-60,000 EWNS per mL of air. In contrast, the inoculated tomatoes exposed to the EWNS and the electric field showed a 2.3 logs removal (1.4 logs compared to the control). This translated to a removal rate of 0.028 logs/min that is approximately three times that of the controls. The inoculated tomatoes in the control treatment showed a decay of approximately 0.9 logs after 90 minutes, which represents a removal rate of 0.008 logs/min for 42,000-60,000 EWNS per mL of air.

The EPES system showed a definite increase in the inactivation of *E. coli* by doubling the efficiency as compared to the inactivation observed for diffusion alone as EWNs are drawn through the chamber when the electric field is applied. Since we can calculate the number of particles that have been deposited in the chamber the results can be viewed as dose response curve assuming that at any time point, the same fraction of EWNS impacts the bacteria. On the contrary, the absence of the electric field and diffusion only delivery resulted in no inactivation. Particles of this size do not impact due to very low inertia. In this case, the EWNS drift around the tomato and do not interact with the bacteria on the surface of the tomatoes.

Example 4: Optimization of Electrospray and Ionization Conditions for the Generation of EWNS with Enhanced Antimicrobial Properties EWNS Synthesis EWNS were synthesized by concurrently electrospraying and ionizing highly purified water (18 MΩ cm$^{-1}$). Briefly, a high voltage is applied between the electrode and a grounded counter electrode. During the process, two distinct phenomena take place: i) the electrospraying and ii) the ionization of the water. Under specific electric field conditions, the strong electric field between the two electrodes causes negative charges to accumulate on the surface of the condensed water, leading to the formation of the Taylor cone. As a result, highly charged water droplets form and continue to break into smaller particles as the Rayleigh theory. At the same time the high electric field causes some water molecules to split and can strip off electrons (ionization), resulting in a high number of reactive oxygen species (ROS). The concurrently generated, short lived ROS (with a lifespan in the order of nanoseconds) are encapsulated in the EWNS. See, e.g., FIG. 1.

FIGS. 2A-2C describe in detail the experimental setup that was developed and used in the synthesis of the EWNS. The fluid 204 (e.g., purified water; 18 MΩ cm$^{-1}$) was fed through a tube 208 (e.g., Teflon tubing; inner diameter=2 mm) to a conduit 212 (e.g., 30G stainless steel needle). To avoid the stepwise pumping action associated with commonly use syringe pumps, compressed air was used to feed the fluid 204 from fluid source 202 (e.g., an explosion-proof container). The flow of the fluid 204 (e.g., water) is controlled with the pressure of air inside the fluid source 202 as is shown in FIGS. 2A-2C. The conduit 212 can be adjusted (e.g., manually or electronically) to a specific distance from the electrode 216. The electrode 216, can be made of any suitable material and suitable configuration (e.g., polished aluminum disk with an opening in the center to allow for sampling).

Conductivity of the material lays a role on the electric field. Beneath the electrode 216 there is a fluid collection member 220 (e.g., an aluminum sampling funnel) that is connected to the electrode aperture 222 as shown in FIGS. 2A-2C. In order to avoid charge built-up that may impair the particle sampling all the components of system 200 were electrically grounded.

Synthesis Parameters

The EWNS generation system described (e.g., system 200) herein the modification of critical operational parameters to permit the fine-tuning of the EWNS properties. The applied voltage (V), the distance between the needle and counter electrode (L), and the flow of the water through the capillary (φ), were systematically varied in an effort to fine tune EWNS properties. The notation used to indicate the different combinations is [V (kV), L (cm)]. For the purpose of this investigation, the diameter of the aerosol sampling hole (D) was kept at 0.5 inches (1.29 cm). But the diameter can be adjusted as necessary without departing from the spirit of the various embodiments of the present invention.

Due to the finite geometry and asymmetry, the electric field strength cannot be calculated from first principles. Instead the software QuickField™ (Svendborg, Denmark) was used to calculate the electric field. As a reference value for the various configurations, the value of the electric field at the tip of the capillary was used.

EWNS Physicochemical Characterization

Surface charge measurements of EWNS: The output of the EWNS generation system 200 was connected directly to a Scanning Mobility Particle Sizer (SMPS, Model 3936, TSI, Shoreview, Minn.) to measure the particle number concentration, and in parallel to a Faraday Aerosol electrometer (TSI, Model 3068B, Shoreview, Minn.) used to measure the aerosol current, as described in our previous publication. The SMPS and the Aerosol Electrometer were both sampling at 0.5 l/min flow rate (total sampling flow 1 L/min). The particle number concentration and the aerosol current were measured for the duration of 120 s. The measurement was repeated 30 times. From the current measurement the total electric charge of the aerosol was calculated and the average EWNS electric charge was estimated for the given total number of EWNS particles sampled.

Since Relative Humidity (RH) can affect the surface electric charge, temperature and (RH) were maintained constant during the experiments, at 21° C. and 45%, respectively.

Size and lifetime measurements of EWNS: An Atomic Force Microscope (AFM), Asylum MFP-3D (Asylum Research, Santa Barbara, Calif.) and the AC260T probes (Olympus, Tokyo, Japan) were used to measure the size and lifetime of EWNS. The AFM scan rate was 1 Hz and the scanned area 5 μm×5 μm with 256 scan lines. All images were subjected to 1$^{st}$ order image flattening with the Asylum Software (range of 100 nm and threshold of 100 pm for the mask).

The EWNS were directly sprayed on a freshly cleaved mica surface (Ted Pella, Redding, Calif.). The sampling funnel was removed and the mica surface was placed at a 2.0 cm distance from the electrode for an average time of 120 s to avoid particle coalescence and the formation of irregular shaped droplets on the mica surface. The surface was imaged immediately after the spray using AFM. The contact angle of a freshly cleaved, unmodified, mica surface is close to 0°$^{20}$ so the EWNS were spread on the mica surface adopting a dome like shape (Figure S5). The diameter and the height of the spread droplet were measured directly from the AFM topography and used to calculate the volume of the dome-like spread of EWNS. Assuming that airborne EWNS have the same volume, an equivalent diameter can be calculated as follows:

$$d = \sqrt[3]{2h^2\left(3\frac{a^2 + h^2}{2h} - h\right)}, \quad (1)$$

where h is the measured height and a is the measured radius of the spread droplet. In total, 40 droplets were measured using AFM and the EWNS size distribution was constructed. The room air temperature and RH were maintained constant during the experiments at 21° C. and 45%, respectively. The process was repeated for the two different scenarios shown in Table I.

ROS characterization of EWNS: Electron Spin Resonance (ESR) spin trapping was used to detect the presence of short-lived free radical intermediates in the EWNS. Radicals were measured using the addition-type reaction of a short-lived radical with a compound (spin trap) to form a relatively long-lived paramagnetic free radical product (spin adduct), which can then be studied using conventional EPR.

The aerosol was bubbled through a 650 μm Midget bubbler (Ace Glass, Vineland, N.J.) containing a solution of 235 mM DEPMPO (5-(Diethoxyphosphoryl)-5-methyl-1-pyrroline-N-oxide), (Oxis International Inc. Portland, Oreg.). DEPMPO was used instead of the more commonly used 5, 5-dimethyl-1-pyrroline-N-oxide (DMPO) because of the increased stability it offers for spin adducts. The aerosol was bubbled through the spintrap solution for 15 minutes since the spin-trap solution has a lifetime of approximately 15 min. All ESR measurements were conducted using a Bruker EMX spectrometer (Bruker Instruments Inc. Billerica, Mass., USA) and a flat cell assembly. Hyperfine couplings were measured (to 0.1 G) directly from magnetic field separation using potassium tetraperoxochromate ($K_3CrO_8$) and 1,1-diphenyl-2-picrylhydrazyl (DPPH) as reference standards. The Acquisit program (Bruker Instruments Inc. Billerica, Mass., USA) was used for data acquisitions and analyses.

The ROS characterization was performed only for the [−6.5 kV, 4.0 cm] set of operational conditions. The EWNS concentration was measured with the SMPS after considering the EWNS loses in the impinger.

Ozone monitor: Due to the presence of high voltage it is likely that ozone can be produced as it has been reported to our previous publications. The ozone levels were monitored with the 205 Dual Beam Ozone Monitor™ (2B Technologies, Boulder, Co).

Electrostatic Precipitator Exposure System (EPES)

FIG. 2C illustrates the previously developed and characterized "draw through" Electrostatic Precipitation Exposure System (EPES) 226 which can be used for targeted delivery of EWNS on surfaces. The EPES 226 utilizes the electric charge of the EWNS and with the application of an electric field, it can directly "guide" them to the target surface. Details of the EPES system 226 are discussed in greater detail in G. Pyrgiotakis, et al., *Environ. Sci. Technol.* 49: 3737-3745 (2015), which is incorporated by reference as if fully set forth herein. Briefly, in some examples the EPES 226 consists of a chamber 229 (e.g., PVC chamber), which has tapered ends 230*a* and 230*b* and contains two parallel plates 231*a* and 231*b* (e.g., stainless steel metal plates such as stainless steel 304, mirror finish) in the center, placed at distance g from one another (e.g., 15.24 cm apart). The plates 231*a* and 231*b* are connected to voltage source 228 (Bertran 205B-10R, Spellman, Hauppauge, N.Y.), with the plate 231*a* connected to positive voltage and the plate 231*b* connected to ground (e.g., floating ground). In some examples, the outside walls 232*a-d* of the chamber were coated with a metal foil (e.g., aluminum foil) that was electrically grounded to prevent particle loses. The chamber 227 has, in some examples, a front door (e.g., an airtight front-loading door; not shown) that allows the test surfaces (e.g., produce) to be placed on an elevated surface (e.g., a plastic rack; not shown) that keeps the test surfaces elevated from the plate 231*a* in order to avoid interference from the high voltage.

The deposition efficiency of the EWNS in the EPES was calculated according to the protocols described in G. Pyrgiotakis, et al., *Environ. Sci. Technol.* 49: 3737-3745 (2015), which is incorporated by reference as if fully set forth herein.

In some examples, a second chamber 233 can be connected in series via conduit 234 to the EPES system 226, utilizing a filter 235 (e.g., a HEPA filter) at the inlet 236 to the second chamber 233 to remove the EWNS. This second chamber 233 can be used as a control chamber for pathogen inactivation experiments and has identical atmosphere (T and RH) as the EPES, but without the EWNS. See FIG. 2C, where, for example, produce 237 is placed.

Bacterial Inactivation Protocols

Important food related microorganisms found to contaminate fresh produce such as *Escherichia coli* (ATCC #27325), *Salmonella enterica* (ATCC #53647), *Listeria inocula* (ATCC #33090), *Saccharomyces cerevisiae* (ATCC #4098) and *Mycobacterium parafortuitum* (ATCC #19686) were procured from ATCC (Manassas, Va.). *E. coli* gains entry into fresh produce from fecal contamination of water source used in washes. *L. innocua* is commonly found in soil and water, *S. enterica* is found in food contaminated with animal fecal matter, like manure. *M. parafortuitum* finds its way into food through contaminated water sources.

Random boxes of organic grape tomatoes were bought from the local market and refrigerated at 4° C. until use (maximum of 3 days). The tomatoes were selected to be of the same size, approximately ½ inch in diameter.

The culture, inoculation, exposure, and colony enumeration protocols have been described in detail in G. Pyrgiotakis, et al., *Environ. Sci. Technol.* 49: 3737-3745 (2015), which is incorporated by reference as if fully set forth herein. Briefly, the spot inoculated tomatoes were exposed for 45 minutes to 40,000 EWNs $\#/cm^3$. Three tomatoes were used to assess the surviving microorganism concentration after 45 minutes of exposure. In addition to the exposed tomatoes, three more were used as control (control chamber/unexposed) and three more for time 0 minutes. Each tomato was plated in triplicate. The data analysis was done according to the protocol described in the supplemental data.

Assessment of Microorganism Inactivation Mechanism

Transmission Electron Microscopy (TEM) Imaging: The EWNS exposed (45 minutes at EWNS aerosol concentration of 40,000 $\#/cm^3$) and the unexposed bacterial samples of *E. coli, S. enterica* and *L. innocua* were pelleted to assess the inactivation mechanism. The pellets were fixed for 2 hours at RT in 2.5% glutaraldehyde, 1.25% paraformaldehyde, and 0.03% picric acid in 0.1 M sodium cacodylate buffer (pH7.4) fixative. After washing they were post fixed with 1% osmium tetroxide ($OsO_4$)/1.5% potassium ferrocyanide ($KFeCN_6$) for 2 h, washed in water 3 times and incubated in 1% uranyl acetate for 1 h followed by two washes in water and subsequent dehydration for 10 minutes each in 50%, 70%, 90%, 100% alcohol. The samples were then put in propyleneoxide for 1 h and infiltrated in a 1:1 mixture of propyleneoxide and TAAP Epon (Marivac Canada Inc. St. Laurent, Calif.). The samples were embedded in TAAB Epon and polymerized at 60° C. for 48 h. The solidified pelleted resins were sliced and imaged by TEM using JEOL 1200EX (JEOL, Tokyo, Japan), a conventional transmission electron microscope equipped with an AMT 2 k CCD camera (Advanced Microscopy Techniques, Corp., Woburn, Mass., USA).

Enzymatic Assays: Assessment of ROS activity was also investigated with enzymatic assays. Two assays were used to apportion the ROS activity from the presence of superoxides and hydroxyl radicals: 1) The activity of the superoxides encapsulated in the EWNS was evaluated with the dismutase (SOD) assay (Dojindo Inc., USA); 2) the activity of the hydroxyl radicals was evaluated with a Catalase peroxidase assay. The assays were executed according the manufacturers protocol and their value was determined colorimetrically. In more detail:

E. coli was inoculated on the tomato surface and subjected to the EWNS for 45 minutes as described before. The tomatoes were vigorously vortexed and washed in 15 ml 1×PBS. The wash solution was centrifuged at 3000×g for 30 minutes and the bacteria were pelleted, the pellet was resuspended in sterile PBS and the enzymatic assays were executed. The live cells were counted via plating the same bacterial suspension as described above to ensure inactivation.

Results

Physicochemical Characterization of EWNS

During the investigation several combinations of the voltage and the distance between the needle and the counter electrode, were evaluated (data not shown). Among them two were the most stable and reproducible and were selected for the complete property investigation (Table 1).

consumption). It is also worth noting that during the EWNS production the ozone levels were very low and never exceeded the 60 ppb levels.

Electric Field: The strength of the electric field is related to the voltage and the distance between the needle and the counter electrode, and the overall geometry. The maximum value of the electric field at tip of the needle can be used as a reference of the electric field strength and for both scenarios. The field was calculated to be $2 \times 10^5$ V/m, and $4.7 \times 10^5$ V/m for the [−6.5 kV, 4.0 cm] and [−3.8 kV, 0.5 cm] scenarios respectively. This is expected since the voltage distance ratio is significantly higher for the second case.

Figure 4:
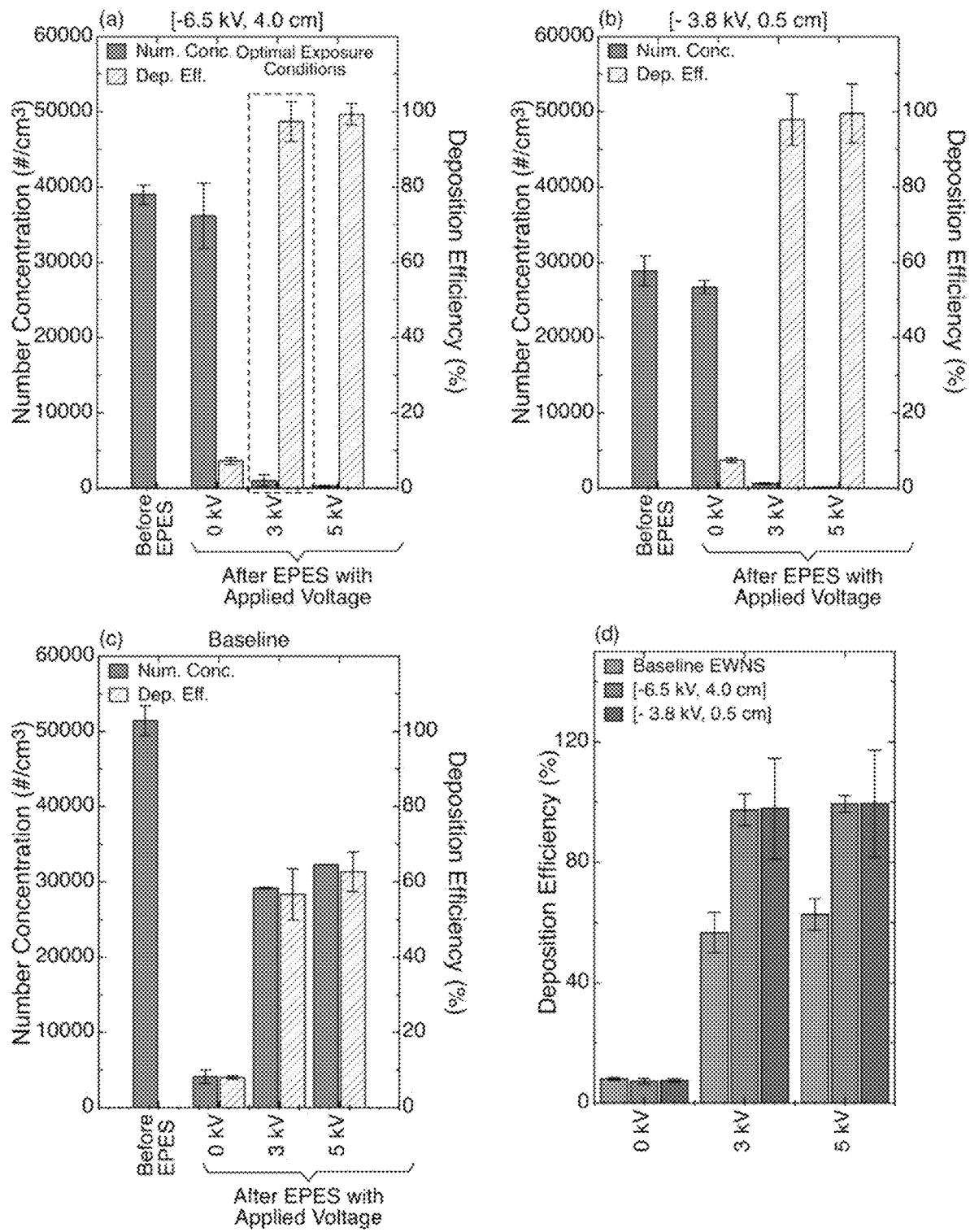
FIG. 4 is a series of plots showing the deposition of the EWNS of the various embodiments of the present invention in a sample electrostatic precipitation exposure system (EPES): (a) [−6.5 kV, 4.0 cm]; (b) [−3.8 kV, 0.5 cm]; (c) "baseline" EWNS; and (d) collective representations of the deposition efficiency of all reported cases.

EWNS Size: FIG. 4 shows the estimated EWNS diameter as it is measured with the AFM. Following the method described above the average EWNS diameter was calculated to 27.36 nm and 19.33 nm respectively for the [−6.5 kV, 4.0 cm] and [−3.8 kV, 0.5 cm] scenarios. The geometric standard deviation of the distribution was 1.41 and 1.45 respectively for the [−6.5 kV, 4.0 cm] and [−3.8 kV, 0.5 cm] scenarios, which is indicative of a narrow size distribution. Both the average size and the geometric standard deviation are very close to the baseline, 25 nm and 1.41 respectively.

Figure 3:
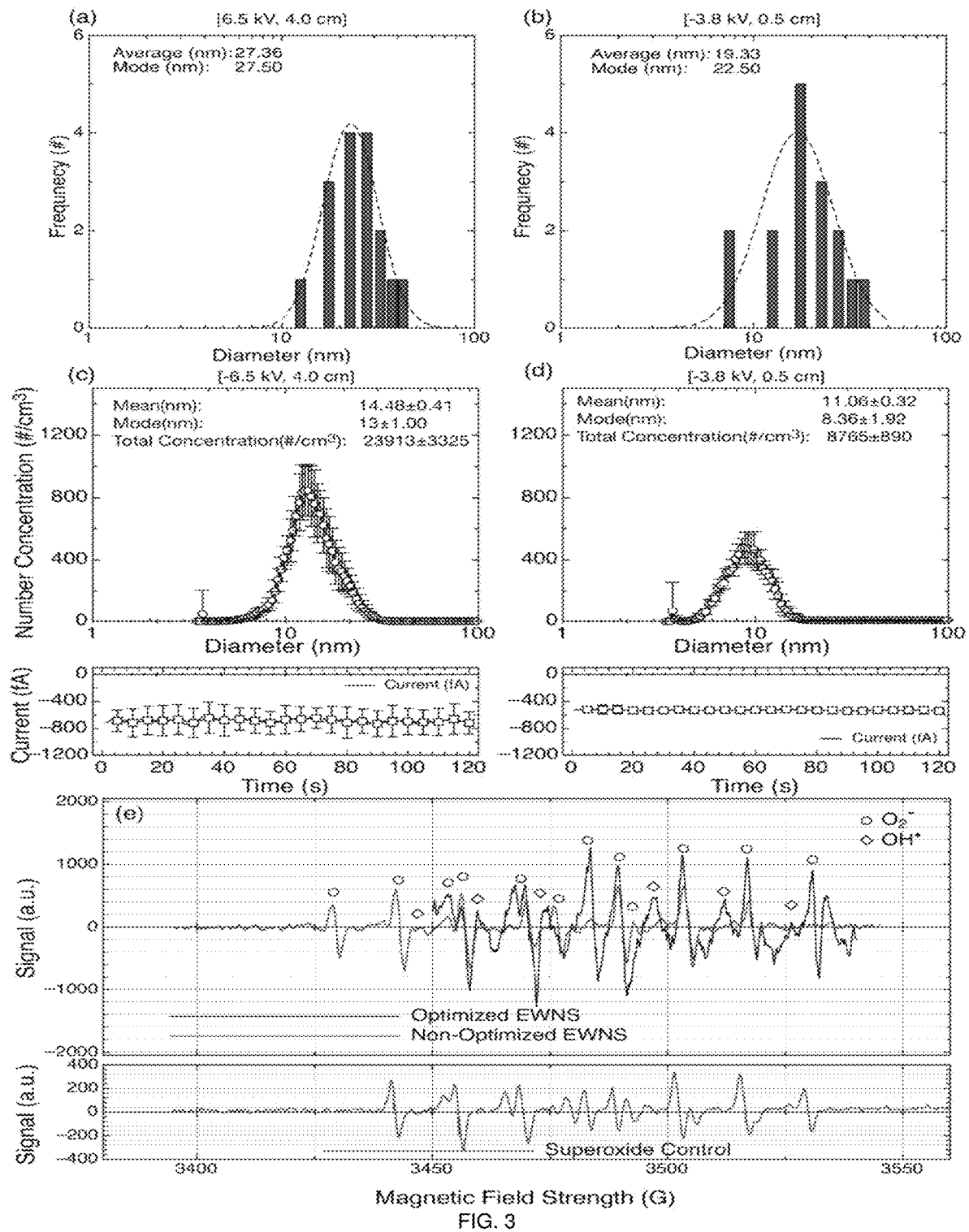
FIG. 3 is a series of plots showing the physicochemical characterization of the EWNS of the various embodiments of the present invention (panels a-b); size distribution of the EWNS of the various embodiments of the present invention as measured with AFM (panels c-d); the surface charge characterization of the EWNS of the various embodiments of the present invention; and the ROS characterization of the EWNS of the various embodiments of the present invention using electron paramagnetic resonance (EPR) spectroscopy.

EWNS electric charge: FIG. 3 shows the results for the charge characterization. The data represent the average measurement of 30 number Concentration (#/cm$^3$) and Current (I) concurrent measurements. The analysis showed that

TABLE 1

| Electrospray/Ionization Conditions | | Electrospray Module Operational Parameters | | | | EWNS Physicochemical characterization Mean | | | Deposition in EPES | |
|---|---|---|---|---|---|---|---|---|---|---|
| Name | Reference | V (kV) | L (cm) | D (cm) | φ (μl/min) | Diameter (nm) | Charge (e$^-$) | ROS | 3 kV 0.5 l/min | 5 kV 0.5 l/min |
| Baseline[†] | [−5.0 kV, 0.5 cm] | −5.0 | 0.5 | 0.40 | [‡] | 25.67 | 10 ± 2 | OH•, O$_2^-$ | 52.18 ± 5.81 | * |
| Condition I | [−6.5 kV, 4.0 cm] | −6.5 | 4.0 | 1.29 | 1.2 | 27.36 | 22 ± 6 | OH•, O$_2^-$ | 97.37 ± 5.26 | 99.32 ± 2.79 |
| Condition II | [−3.8 kV, 0.5 cm] | −3.8 | 0.5 | 1.29 | 0.9 | 19.33 | 44 ± 6 | * | 97.84 ± 6.77 | 99.49 ± 7.83 |

Notation used at the table (also described in FIG. 2):
V: Applied Voltage
L: Distance between counter electrode and needle
D: Counter Electrode sampling diameter
φ: Flow of the water
[†]Different electrode geometry
[‡] Not applicable
* Not investigated FIG. 3 shows in more detail the experimental data results. The supplemental data include an investigation of the effects of counter electrode sampling hole diameter (D) and distance between the grounded electrode and the tip of the needle (L).

It should be mentioned that although the water flow was a parameter of the investigation, it was only adjusted to produce a stable Taylor cone, based on the voltage (V) and the distance between the needle and counter electrode (L) that were selected. Therefore it is not part of the parametric analysis.

It is also important to note that for all the above mentioned conditions the measured ionization electric current was between of 2-6 μA and the voltage was between −3.8 and −6.5 kV, resulting in energy consumption less than 50 mW for this single needle EWNS generation module (low energy the average charge per EWNS is (22±6) e and (44±6) e$^-$ respectively for the [−6.5 kV, 4.0 cm] and [−3.8 kV, 0.5 cm] respectively. As compared to the baseline EWNS have significantly higher surface charge that is two times for the [−6.5 kV, 4.0 cm] scenario and four times higher for the [−3.8 kV, 0.5 cm] case.

EWNS number concentration: It is evident from the EWNS number concentration graphs (FIG. 3) that the particle number for the [−6.5 kV, 4.0 cm] scenario is significantly higher (23913 #/cm$^3$) compared to the [−3.8 kV, 0.5 cm] scenario (8,765 #/cm$^3$) (FIG. 4). It is also worth noting that the EWNS number concentration was monitored for up to 4 hours where the EWNS generation stability showed similar particle number concentration levels for both scenarios. Due to the significantly higher particle number concentration yield the [−6.5 kV, 4.0 cm] scenario was selected for the inactivation experiments and ROS characterization.

ROS Investigation: FIG. 3 shows the ESR spectrum, after subtraction of control (background) of the optimized EWNS for the [−6.5 kV, 4.0 cm]. The ROS spectrum was also compared to that of baseline EWNS scenario from previously published work. The number of the EWNS reacted with the spin trap was calculated, at $7.5 \times 10^4$ EWNS/s which is similar to the one previously reported for the baseline EWNS. The ESR spectrum clearly indicates the presence of two ROS species, with $O_2^-$ being the dominant species, and OH. present in smaller amounts. Further the direct comparison of the peak intensity indicates that the optimized EWNS have significantly higher ROS content compared to the baseline EWNS. However, it should be noted that the optimized EWNS have a larger ratio of OH. to $O_2^-$ (0.48) compared to the baseline EWNS (0.07). EWNS and an increased concentration of OH. was found.

Figure 5:
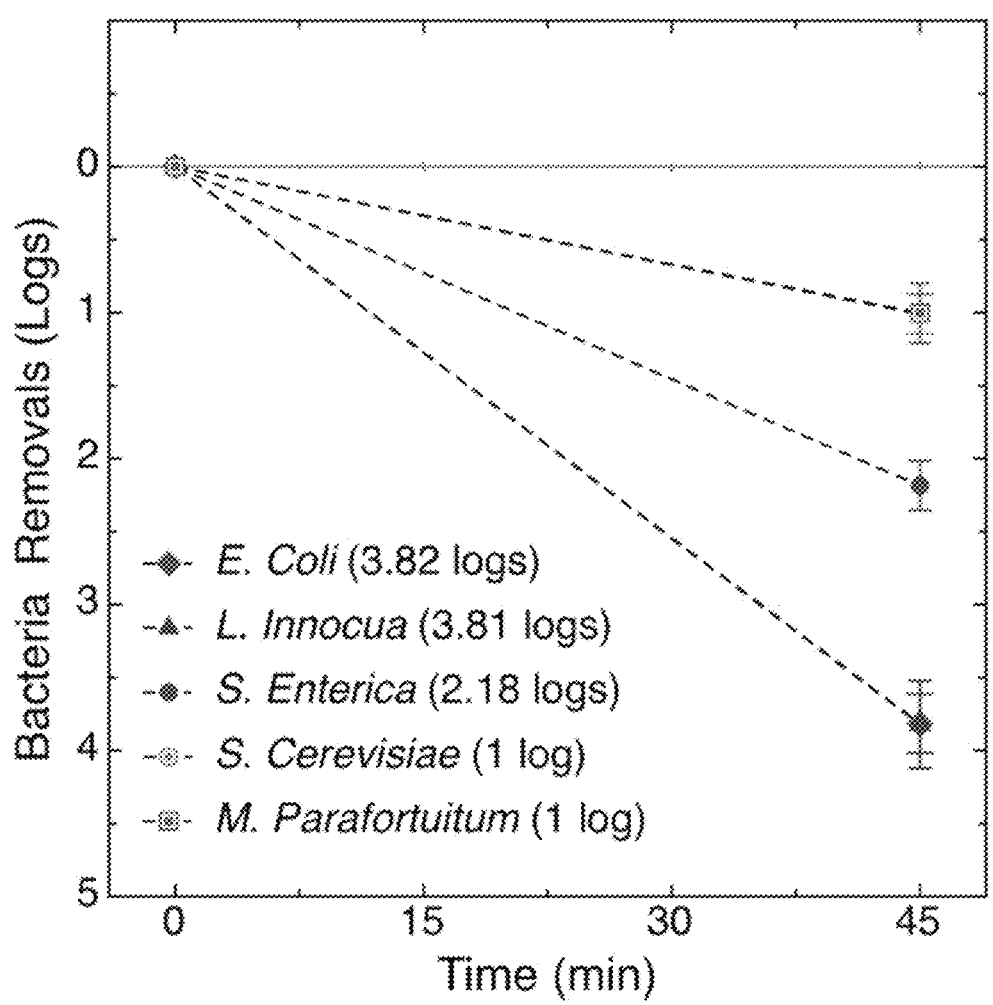
FIG. 5 is a plot of inactivation of bacteria on tomato surface in EPES with EWNS. The data are presented normalized to the control.

EWNS deposition in EPES: FIG. 5 represents the EWNS deposition efficiency in the EPES. The data are also summarized in Table I and compared with the baseline EWNS data. The deposition even for the low voltage of 3 kV is reaching nearly 100% deposition for both cases of the EWNS. Generally, the 3 kV is enough to reach 100% deposition regardless of the variations on the surface charge. It is worth noting that the baseline EWNS had only 56% deposition efficiency because of their lower electric charge (10 electrons per EWNS on average)

Microbial Inactivation

Figure 6:
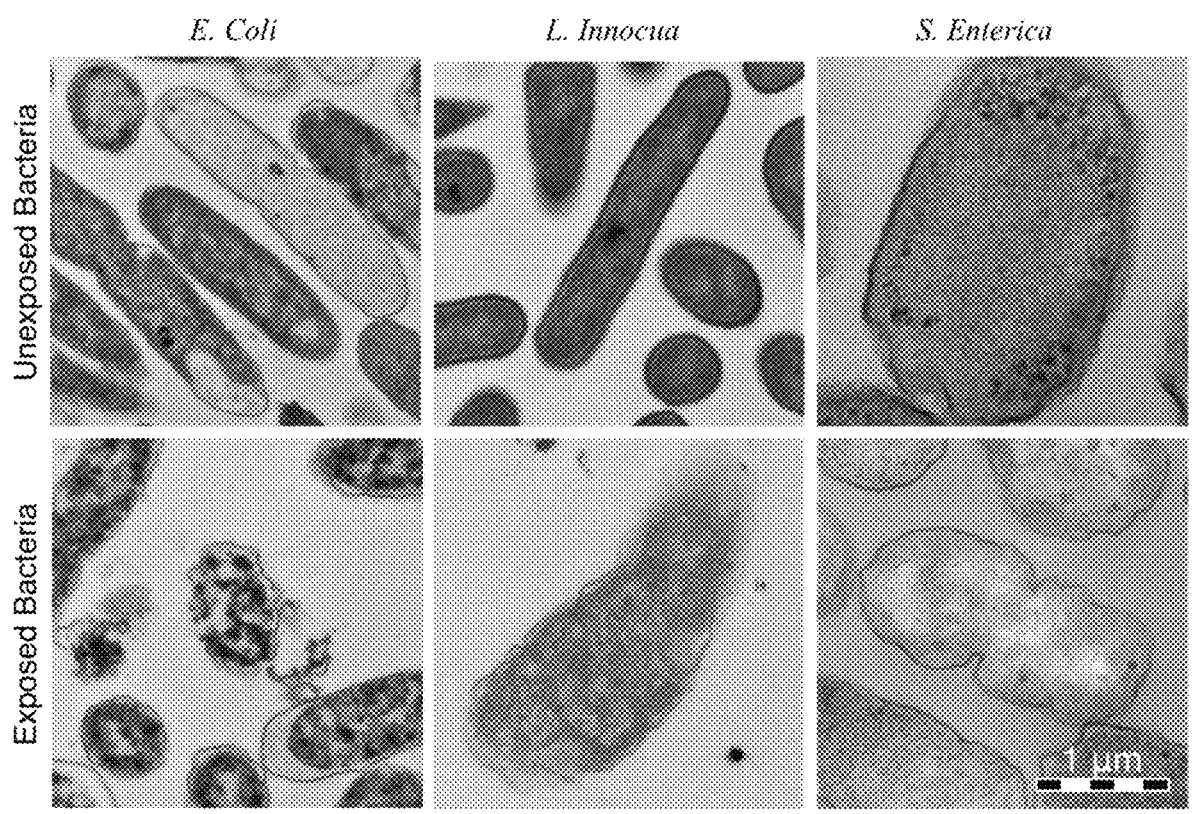
FIG. 6 is a series of electron micrographs showing unexposed bacteria and bacteria exposed to the EWNS of the various embodiments of the present invention.

The inactivation of food related microorganisms inoculated on the tomato surface and the corresponding logs/hr reductions following exposure to approximately 40,000 #/cm³ EWNS are summarized in FIG. 6 and Table 2 for the [−6.5 kV, 4.0 cm] scenario.

Meanwhile the thick glycogen layer is well observed in the control *S. enterica* cells and the exposed cells clearly show damage at various sites of the outer membrane. Lastly, *L. innocua* exposed to EWNS evidently show outer membrane damage when compared to the control unexposed cells.

Enzymatic Assays

Figure 7:
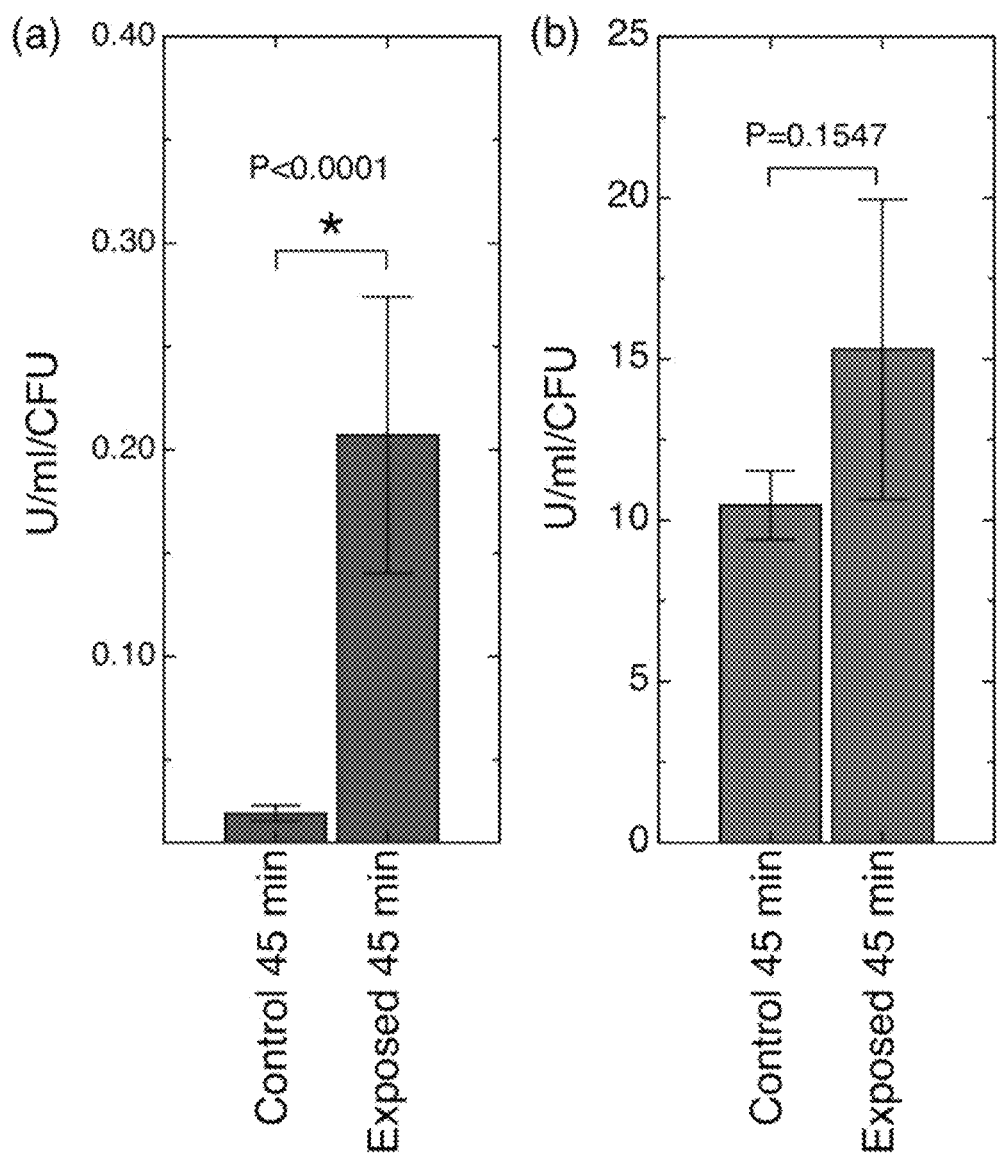
FIG. 7 is a series of plots showing superoxide dismutase activity in *E. coli* exposed to o the EWNS of the various embodiments of the present invention.

The activity of the SOD and the catalase enzymes is shown in FIG. 7. It is evident that the SOD activity (FIG. 7a) was significantly ($P<0.0001$) more compared to the control *E. coli* at 0 and 45 minutes. On the contrary the catalase assay does not show any significant difference between the exposed and the control *E. coli* bacteria.

Discussion

Collectively, the data regarding the physicochemical characterization of the optimized EWNS show that the EWNS properties have been enhanced significantly as compared to previously reported results. See, e.g., G. Pyrgiotakis, et al., *Environ. Sci. Technol.* 49: 3737-3745 (2015), which is incorporated by reference as if fully set forth herein. From the presented data it is evident that both the charge and the ROS content have increased.

As shown in FIG. 3, the EWNS appear to be polydisperse in size and follow a log normal distribution. The observed polydispersity can be explained from the variation of the surface charge, which dictates the size, the randomness of the Rayleigh effect and potential coalescences of the EWNS. The size however is still in the nano regime, very similar to the previously reported results. This is an important parameter, since it is due to that small size that they are able to stay airborne for a long time. In addition, the energy required for the EWNS synthesis is very low, which further exemplifies the green nature of the technology.

Further the surface charge was found to be in the order of 22-44 electrons per structure depending on the settings of the operational synthesis parameters. In our previous work

TABLE 2

| | Exposure at 40,000 #/cm³ | | | |
| --- | --- | --- | --- | --- |
| | Removal Rates | | Removal Rates Compared to control | |
| Pathogen | Logs Rem. | LRR (Logs/hr) | Logs Rem. | LRR (Logs/hr) |
| E. coli | 5.47 | 7.294 ± 0.052 | 3.82 | 5.093 ± 0.137 |
| L. innocua | 5.49 | 7.325 ± 0.046 | 3.81 | 5.079 ± 0.092 |
| S. enterica | 3.56 | 4.747 ± 0.359 | 2.18 | 2.907 ± 0.541 |
| S. cerevisiae | 3.29 | 4.391 ± 0.698 | 1.00 | 1.333 ± 0.082 |
| M. parafortuitum | 2.65 | 3.544 ± 0.918 | 1.01 | 1.333 ± 0.578 |

For the E. co/i, there was a significant 3.82 log reduction of 5.09±0.052 Log/hr (Table 2) Interestingly, similar significant levels of inactivation were also seen for *L. innocua* (3.81 log reduction corresponding to a 5.08±0.046 logs/hr reduction) when exposed to similar levels of EWNS (40 000 #/cm³) at 45 min. At the same conditions, *Salmonella enterica*, however, exhibited lower log reductions (2.18 log reduction resulting in a 2.90±0.359 logs/hr. Both *S. cerevisiae* and *M. parafortuitum* showed only a 1 log reduction at the 45 min mark resulting to 1.333±0.698 logs/hr log reduction.

Mechanism of Microorganism Inactivation

Electron micrographs (FIG. 6) depict the inactivation of *E. coli, S. enterica* and *L. innocua* by EWNS. The control E. co/i cells appeared normal and had an intact internal structure and outer membrane, whereas the cells exposed to EWNS appeared to have their outer membrane damaged.

for the baseline EWNS, a charge of 10±2 electrons per structure was found. It should be noted, that this represents the average charge of the EWNS. Seto et al. have shown that the charge is not uniform and follows a log-normal distribution. Further, as compared to our previous work, the doubling surface charge doubles the deposition efficiency in the EPES system, reaching an almost 100% (FIG. 4).

The optimization of the synthesis parameters, also affects the ROS content. As it can be seen from the direct comparison of the EPR spectra (optimized EWNS vs. previously reported baseline EWNS), both EWNS aerosols contain hydroxyl and superoxide radicals. Although the exact concentration cannot be determined, the peak intensity is proportional to the hydroxyl and peroxide concentration. It is very clear therefore that the peak intensity of the optimized EWNS is higher, which means that the optimized EWNS have significantly higher ROS content. Although the direct measurement of the lifetime of the ROS within the EWNS remains technically a challenge, the presence of ROS in EWNS after their synthesis was indirectly confirmed in a previous study, since the inactivation of pathogens occurred up to 38 minutes after their production.

Further the ozone levels were below 60 ppb, which is expected due to the lower voltage that is being applied in the current synthesis system. This is an important improvement since it is eliminating the need of ozone scrubbers, as these levels are below the EPA allowed levels of about 72 ppb for a maximum of about 8 hours.

The bacteria inactivation data illustrate that even with a fairly low dose of 40 000 #/cm$^3$ generated from a single needle electrospray module used here, there is a strong inactivation for *E. coli* and *L. innocua* (approximately 4 logs removal at 45 minutes of exposure), less, yet significant inactivation for the *S. enterica* (approximately 2 log removal) while for the yeast and *M. parafortuitum* the inactivation was the lowest observed. The 2 logs difference in the inactivation between *S. enterica* and *E. coli* seems contradictory since both are gram-negative bacteria with similar cell structure. However, *Salmonella* has a high glycogen content, which makes the bacterial cell-wall thicker and more difficult to disrupt. This was confirmed also with the TEM images that revealed the glycogen layer (FIG. 6). Furthermore *mycobacterium* is known for its very thick lipid layer that protects it from harmful conditions like ROS, UV or other oxidizing source making it a more resilient microorganism to inactivate.

It is worth noting that the results published in our previous work the baseline EWNS achieved an inactivation rate of *E. coli* at 0.95 logs/hr (0.716 logs in 45 minutes), while with the optimized EWNS in this study, the log removal rate skyrocketed at 5.09 logs/hr (3.82 logs in 45 minutes) at similar EWNS concentration levels. The five-fold increased inactivation efficacy observed in this study can be attributed to the optimization of the EWNS properties. The increased electric charge for the optimized EWNS (22 e/particle) compared to the baseline EWNS (10 e/particle) has an effect on the deposition efficiency in the EPES system (the deposition efficiency increased from 56% to 99%). That alone may explain some of the increased inactivation potential for the optimized EWNS used in this study. However, even when the inactivation potential was normalized per particle delivered (which are $2\times10^7$ #/min for optimized EWNS and $5\times10^7$ #/min for previously reported EWNS) there is a significant inactivation difference between the two EWNS particle systems. The optimized EWNS result into $2.545\times10^{-7}$ logs/EWNS, while the previously reported baseline EWNS data show $0.336\times10^{-7}$ logs/EWNS. It is evident that there is approximately 8 times higher inactivation potential from the optimized EWNS, aside from the higher deposition efficiency, indicative of a higher ROS content, as shown in the property characterization section above. It should be mentioned that similar trends are observed for the inactivation of *Listeria* which was also tested in our previous work. It is clear therefore, that both the higher deposition rate and the increased ROS concentration of the optimized EWNS have both contributed to the higher observed inactivation rates as compared to the previously reported EWNS.

Typical chemical treatment of fresh produce such as peroxyacetic acid (PAA) and chlorine wash can inactive *E. coli* O157:H7, *Listeria* and *Salmonella* spp. by achieving 1-3 logs removal within 3 minutes. However, both chemicals leave behind chemical residues, are toxic and can be only applied at certain points in the farm to fork continuum, usually at post harvest/packaging. On the contrary, EWNS can be used as a continuous disinfection at all CCP of the food production chain, including transportation, storage and marketplace displays, all points that can introduce microbial contaminations compromising prior attempts to reduce the present of contaminants. The inactivation is dose dependent. Accordingly, scaling up the generation system to increase the EWNS generation concentration levels will result to higher inactivation reductions and may shorten the required exposure time.

These experiments clearly show that high levels of ROS can cause stress conditions in gram-negative microorganisms by augmenting irreversible damage to cellular components due to reduction of cell stability and modification of proteins. The three pathogens *E. coli, S. enterica* and *L. innocua* exposed to EWNS revealed badly damaged cells that were indicative of aberrant morphology (FIG. 6). They display cracked and ruptured outer membrane when compared to the control cells that had intact outer membrane, clearly defined periplasmic space, and intercellular structure. The ROS accumulated in the membrane is known to penetrate the cell and cause deformation and damage of the outer membrane which ultimately can result in cell lysis. The localized and structural defects leading to bulging of cell wall that limits the peptidoglycan defects restricting peptide cross linking in gram-negative bacteria; accounts for the significant log reduction counts for all the three pathogens (FIG. 5).

The ROS play an integral role in bacterial metabolism that regulates the endogenous production of enzymes like catalases, peroxidases and SODs which scavenge the superoxide radicals and maintain over all bacterial metabolism. As a part of its adaptive response to oxidative stress, *E. coli's* outer membrane proteins detect the presence of ROS content in their environment. When ROS is detected activation of repair systems like; SOD system and catalase-peroxidase systems occurs. Catalases is typically inactivating the OH., while the SOD is inactivating the $O_2^-$.

The SOD assay shows (FIG. 7) the SOD enzyme is significantly upregulated in the presence of EWNS when compared to the unexposed control, which indicates the presence of peroxide. On the contrary the hydroxyl radicals that are typically neutralized by the Catalases have no significant difference between the exposed as compared to the control, indicating that there are no detectable amounts of hydroxyl radicals. These results are in agreement with previously published data that indicate that the superoxide radicals are involved in mechanism of death of microorganisms when exposed to EWNS. In our previous publication the destruction of the lipid membrane was clearly shown, and a lipid peroxidation assays (LPO) identified the ROS as the primary mechanism of inactivation. However, it was not clear which of the two species was responsible for the inactivation. Here it is clearly shown that the superoxide ROS is the primary method of inactivation. These results are in accordance with the data regarding the ROS content and concentration (FIG. 3), that showed that the superoxide ROS are the dominant species in the EWNS.

In conclusion, the optimized EWNS properties resulted in higher ROS content and deposition efficiency and in higher microorganism inactivation potential as compared to the previously published baseline EWNS. The technology consumes very little energy (less than 50 mW for a single needle generation module), and leaves no chemical residue, which makes it a green sustainable antimicrobial platform. Future studies will focus on the development of a high throughput EWNS generation system using a multi-needle approach to increase the EWNS aerosol concentration output and achieve even higher inactivation in shorter exposure time.

Figure 8:
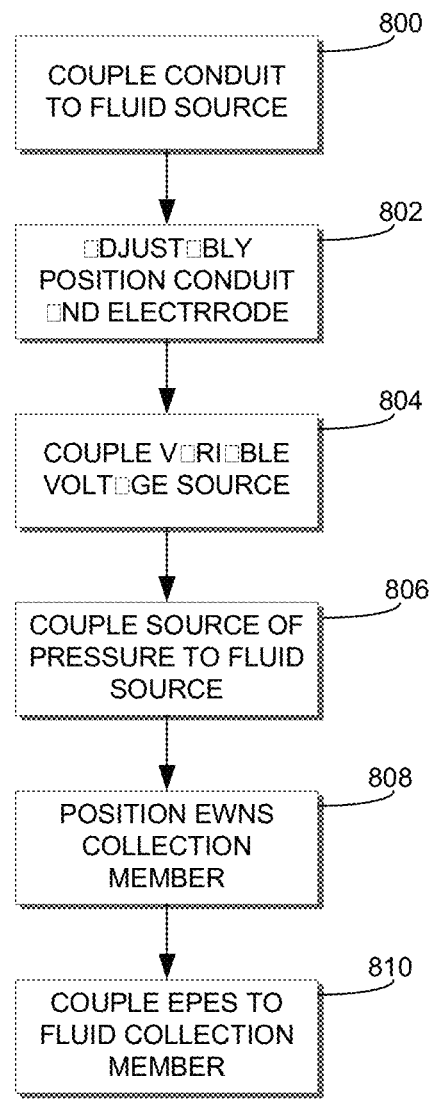
FIG. 8 is a flowchart for making a system used for making and using EWNS.

FIG. 8 is a flowchart for making the system 200, in an example embodiment.

At 800, a conduit is coupled to a fluid source configured to contain a fluid, the conduit forming an aperture.

At 802, the conduit is adjustably positioned with respect to an electrode to set a predetermined adjustable distance from the aperture to the electrode. In an example, adjustably positioning the conduit includes positioning the aperture is above and substantially along a vertical axis with respect to the electrode. In an example, at least some of the engineered water nanostructures fall onto the electrode. In an example, adjustably positioning the conduit is along the vertical axis to set the predetermined adjustable distance.

At 804, a variable voltage source is electrically coupled between the conduit and the electrode, the variable voltage source configured to impart an electric potential difference between the conduit and the electrode. Fluid from the fluid source that passes through conduit and the aperture is changed to engineered water nanostructures upon coming into proximity of the electrode based on the predetermined distance and the electric potential. In an example, the electrode forms an electrode aperture and wherein the engineered water nanostructures comes into proximity of the electrode by passing through the electrode aperture. In an example, the conduit is formed of an electrically conductive material, the voltage source is coupled to the electrically conductive material, and the electric potential difference between the aperture and the electrode induces an electric field between the aperture and the electrode through which the fluid passes. In an example, the conduit is a metallic capillary. In an example, the metallic capillary has a first end and a second end opposite the first end, wherein the first end is coupled to the fluid source and the aperture is at the second end.

At 806, a source of pressure is coupled to the fluid source, the source of pressure configured to place fluid in the fluid source under pressure to force the fluid into the conduit.

At 808, an engineered water nanostructure collection member is positioned with respect to the electrode, wherein engineered water nanostructures that contact the electrode are collected by the engineered water nanostructure collection member.

At 810, an electrostatic precipitator exposure system is fluidly coupled to the fluid collection member, the electrostatic precipitator exposure system configured to apply engineered water nanostructure as collected by the fluid collection member to a target.

What is claimed is:

1. A method for inactivating at least one of bacteria, mycobacteria, bacterial spores, and fungi on foodstuffs comprising:
contacting the foodstuffs with engineered water nanostructures (EWNS) comprising reactive oxygen species (ROS) and an electric charge from about 20 to about 100 e−; wherein the electric charge of the EWNS is an average EWNS electric charge of a sample of EWNS, the average EWNS electric charge determinable by parallel measurement of the aerosol current and the particle number concentration of the sample of EWNS and the contacting inactivates the at least one of bacteria, mycobacteria, bacterial spores, and fungi located on the foodstuffs.

2. The method of claim 1, wherein the foodstuffs is produce or meat.

3. The method of claim 1, wherein the bacteria are at least one of gram-positive and gram-negative bacteria.

4. The method of claim 1, wherein the bacteria are selected from the group consisting of *E. coli*, *Salmonella* bacterial strains, *Listeria* bacterial strains, and *Campylobacter* and *Clostridium* bacterial strains.

5. The method of claim 1, wherein the produce comprises tomatoes, cucumbers, and peppers.

6. The method of claim 1, wherein the EWNS are applied to the foodstuffs at a concentration of about 5,000 to about 500,000 EWNS per mL.

7. The method of claim 1, wherein the EWNS are applied for about 10 minutes to about 180 minutes.

8. The method of claim 1, wherein the inactivating comprises reducing the number of colony forming units (cfu) on the foodstuffs by about 1 to about 6 $\log_{10}$ compared to control.

9. The method of claim 1, wherein the inactivating comprises reducing the number of colony forming units (cfu) on the foodstuffs at a rate of from about 1 $\log_{10}/h$ to about 6 $\log_{10}/h$, compared to control.

10. The method of claim 1, wherein the applying efficiency is from about 90% to about 100%.

11. The method of claim 1, wherein the applying comprises applying the EWNS by electrostatic precipitation or diffusion.

12. The method of claim 1, wherein the ROS comprise hydroxide radicals (OH.) and superoxide ($O_2^-$).

13. The method of claim 1, wherein the method does not cause any or substantially any deterioration in a sensory quality of the produce.

14. The method of claim 13, wherein the sensory quality of the produce is at least one of texture, color, and aroma.

* * * * *